(12) United States Patent
Ozaki et al.

(10) Patent No.: US 7,368,083 B2
(45) Date of Patent: May 6, 2008

(54) BLOOD PROCESSING APPARATUS AND BLOOD INTRODUCING METHOD

(75) Inventors: Nobuhiko Ozaki, Nara (JP); Hiroaki Oka, Osaka (JP); Tetsuo Yukimasa, Nara (JP); Hidenobu Yaku, Osaka (JP); Maki Yotsuhashi, Osaka (JP); Yukari Hataoka, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 124 days.

(21) Appl. No.: 11/494,749

(22) Filed: Jul. 28, 2006

(65) Prior Publication Data

US 2006/0263247 A1 Nov. 23, 2006

Related U.S. Application Data

(63) Continuation of application No. PCT/JP2005/022163, filed on Dec. 2, 2005.

(30) Foreign Application Priority Data

Jan. 28, 2005 (JP) ............... 2005-020781

(51) Int. Cl.
*G01N 33/00* (2006.01)
(52) U.S. Cl. ............ 422/73; 422/63; 422/64; 422/65; 422/67; 422/72; 422/99; 422/100; 436/45; 436/180
(58) Field of Classification Search ............ 422/63–67, 422/72–73, 99–100; 436/45, 180
See application file for complete search history.

(56) References Cited

U.S. PATENT DOCUMENTS 5,460,974 A 10/1995 Kozak et al.

2005/0072670 A1 4/2005 Hasegawa et al.

FOREIGN PATENT DOCUMENTS

| EP | 0 597 268 A1 | 5/1994 |
|---|---|---|
| EP | 1 482 307 A | 12/2004 |
| JP | 6-201704 A | 7/1994 |
| JP | 2000-65778 A | 3/2000 |
| JP | 2000-514928 A | 11/2000 |
| JP | 2000-515632 A | 11/2000 |
| JP | 2001-503854 A | 3/2001 |
| JP | 2002-503331 A | 1/2002 |
| JP | 2002-196001 A | 7/2002 |
| JP | 3356784 | 10/2002 |
| JP | 2003-185566 A | 7/2003 |
| JP | 2003-254933 A | 9/2003 |
| JP | 3469585 | 9/2003 |
| WO | WO 03/074999 A1 | 9/2003 |

OTHER PUBLICATIONS

International Preliminary Report on Patentability, issued in corresponding International Patent Application No. PCT/JP2005/022163, dated on Aug. 9, 2007.

*Primary Examiner*—Jill Warden
*Assistant Examiner*—Jyoti Nagpaul
(74) *Attorney, Agent, or Firm*—McDermott Will & Emery LLP

(57) ABSTRACT

The present invention provides a blood processing apparatus that can introduce a metered quantity of a blood sample into a chamber and does not require an opening linked to the chamber to be closed after the introduction of the blood sample. An introducing chamber, an injection port, and an air port are formed in a rotatable platform of a blood processing apparatus. The injection port links the introducing chamber with the outside of the rotatable platform. A blood sample is introduced from the injection port into the introducing chamber. A blood coagulant is held on the port wall surface of the air port and/or around a portion of the surface of the rotatable platform where the air port is open.

16 Claims, 22 Drawing Sheets

Fig. 4
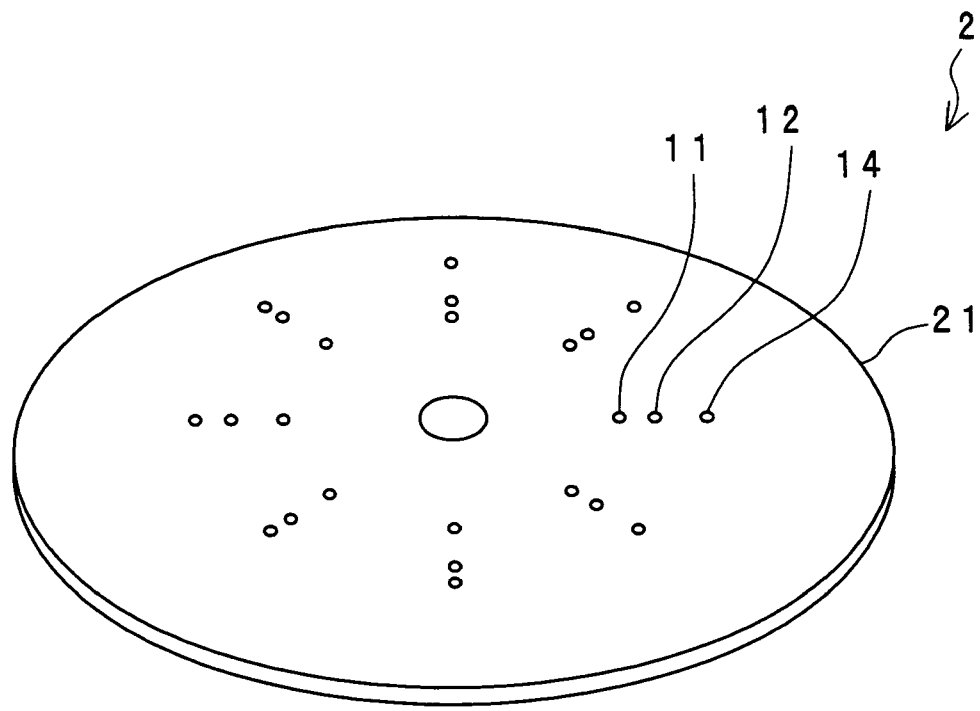
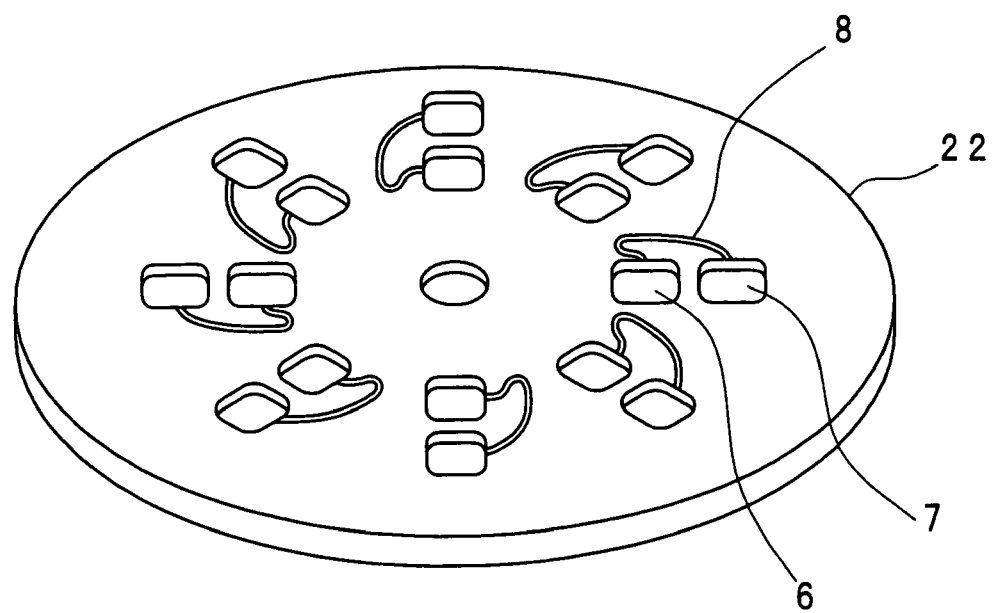

Fig. 11
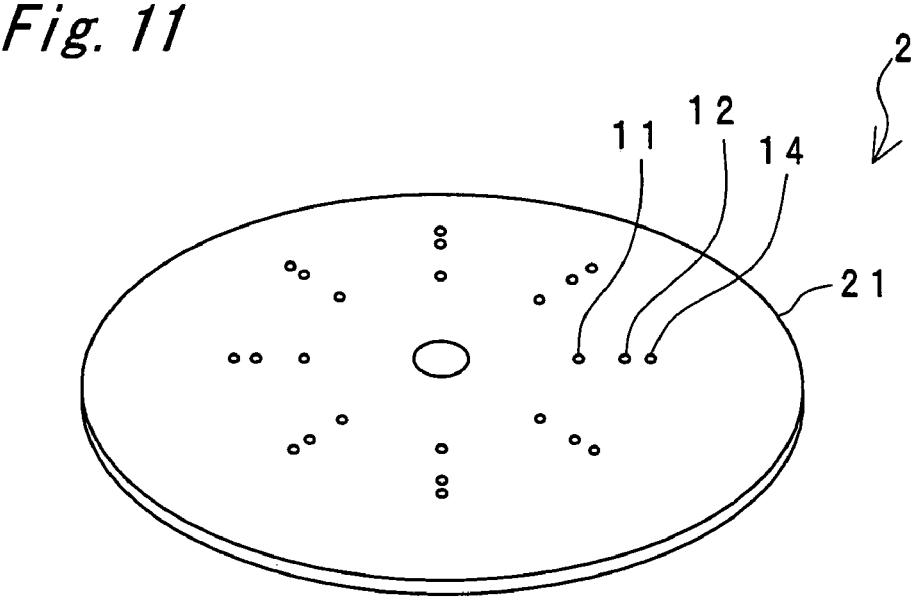
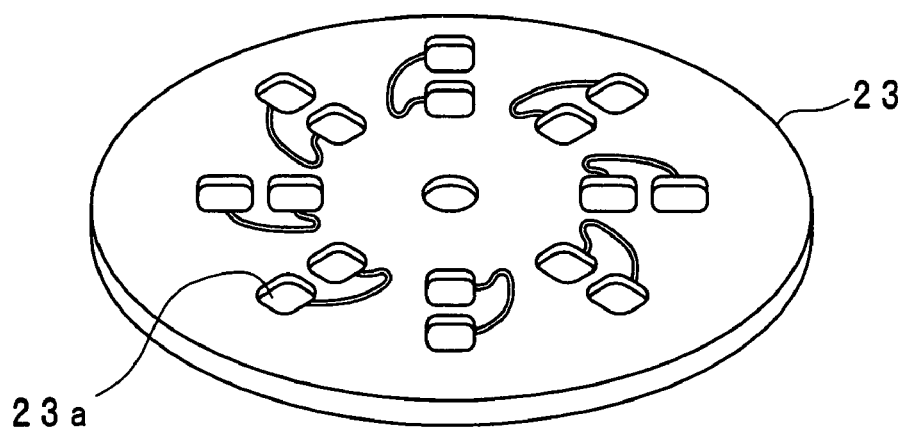
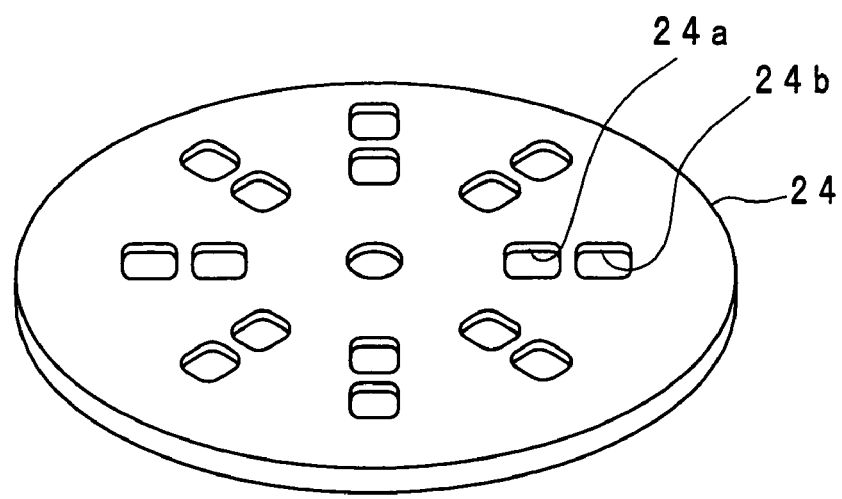

BLOOD PROCESSING APPARATUS AND BLOOD INTRODUCING METHOD

This is a continuous application of International Application No. PCT/JP2005/22163, filed Dec. 2, 2005.

BACKGROUND OF THE INVENTION

The present invention relates to a blood processing apparatus and a method for introducing blood into the blood processing apparatus. More particularly, the present invention relates to a blood processing apparatus comprising a chamber for introducing a metered quantity of a blood sample, so as to conduct various operations with respect to the blood such as analysis of blood components, e.g., electrochemical analysis of protein components contained in blood plasma, or blood cells—blood plasma separation. The present invention also relates to a method for introducing a blood sample into the chamber of such blood processing apparatus.

A variety of health diagnostic chips have recently been developed. Practically all the health diagnostic chips are card-type devices having a micro fluid passage structure called a MICROTAS (μ-TAS: Micro Total Analysis System). The transition to micro fluid passages is very useful because microscopic amounts of samples can be extracted from a living body. Furthermore, if the entire apparatus comprising a health diagnostic chip is miniaturized by employing microscopic fluid passages, the apparatus can be used not only in comparatively large hospitals, but also for POCT (Point Of Care Test: field diagnostics thereof) applications for conducting diagnostics in medical offices and at home.

The analysis object in the devices of this type is usually blood. Blood is a viscous liquid comprising blood cell, which are a particulate component, and blood plasma, which is a liquid component. Because a viscous blood sample is difficult to introduce into a micro fluid passage, a variety of attempts have been made to introduce the blood into micro fluid passages.

FIG. 20 shows a biosensor for electrochemically measuring a blood sugar value in a blood disclosed in Japanese Patent Application Laid-open No. 2000-065778. This biosensor has a structure in which a spacer 102 is sandwiched between two platforms 101, 103. A slit 104 for introducing blood that is formed in the spacer 102 is hydrophilized. Measurement electrodes 106, 107, 108 are disposed in the vicinity of an entry port 104a of the slit 104. Furthermore, an air port 105 is provided in the vicinity of a closed end 104b of the slit 104. The entry port 104a, electrodes 106 to 108, and air port 105 are arranged in a row in the order of description along the extension direction of the slit 104.

The blood sample introduced from the entry port 104a flows toward the electrodes 106 to 108 due to a capillary phenomenon inside the hydrophilized slit 104. Because the air present inside the slit 104 escapes to the side opposite that of the entry port 104 and is drained from the air port 105, the slit 104 can be filled with the blood sample up to the closed end 104b of the slit. Therefore, air bubbles do not remain (air bite does not occur) in the zone of the slit 104 corresponding to the electrodes 106 to 108. Furthermore, the volume of the blood sample introduced into the slit 104 can be quantitatively estimated. For those two reasons the electric signal obtained with the electrodes 106 to 108 has good reproducibility, and the quantity of sugar contained in the blood can be quantitatively determined. The structure in which the air port 104a is provided in the slit 104 is very important for introducing microquantities of solution into a microslit or micro fluid passage with a microliter volume of at least one representative length of several hundreds of micrometers to several millimeters.

In the biosensor shown in FIG. 20, because the electrodes 106 to 108 are positioned above the slit 104, it is not necessary to deliver the blood sample. However, certain measurements require the blood to be delivered or pretreated. For example, when CRP (C reactive proteins) contained in blood are measured electrochemically, blood cells are an inhibiting factor for measurements. Therefore, blood cells—blood plasma separation has to be carried out and the separated blood plasma component solution has to be measured. A method using a centrifugal force is one of the liquid delivery methods suitable for POCT applications.

The biosensor disclosed in Japanese Patent Application Tokuhyo No. 2001-503854 uses a centrifugal force generated by rotating a platform as a drive source for liquid delivery, and a solution can be delivered from one chamber to another chamber via a micro fluid passage. The delivery is based on the following principle. When the platform is not rotated, the liquid is held inside the chamber by surface tension generated on the interface of the chamber and micro fluid passage, but a centrifugal force generated by the rotation of the substrate disrupts the balance of forces and delivers the liquid to the other chamber. With this liquid delivery method, by contrast with the delivery using a pump, connecting a tube is not necessary. Therefore, a dead volume required to move the liquid is not produced. Furthermore, if a large number of fluid passages are provided in the platform, then a plurality of liquid delivery operations can be executed in parallel. Moreover, the above-described blood cell-blood plasma separation also can be realized with a centrifugal force. More specifically, because of a difference in density between the blood cells, which are a particulate component, and blood plasma, which is a liquid component, they can be separated from each other by a centrifugal force. Therefore, the liquid delivery method using a centrifugal force as a drive source, which is disclosed in Japanese Patent Application Tokuhyo No. 2001-503854, can be unified with blood cell-blood plasma separation. More specifically, both the blood cell-blood plasma separation in one chamber and the delivery of the separated blood plasma component solution into another chamber via a micro fluid passage can be realized by a centrifugal force. Japanese Patent Application Tokuhyo No. 2002-503331 and Japanese Patents No. 3356784 and 3469585 disclose liquid delivery methods using a centrifugal force.

However, the following problem is associated with air draining during blood sample introduction when a centrifugal force is used for blood cell-blood plasma separation and delivery.

Referring to FIG. 21, when no air port (see reference numeral 105 in FIG. 20) is provided in the chamber 200 for introducing the blood sample and a micro fluid passage 201 for delivery into another chamber (not shown in the figure) is caused to function as an air port, a limitation is placed on the position where the micro fluid passage 201 can be connected to the chamber 200. First, because the centrifugal force generated during rotation of the platform 202 acts in the direction of withdrawing from the rotary shaft 203, as shown by an arrow, an injection port 204 for injecting the blood sample into the chamber 200 has to be provided on the inner peripheral side (centripetal direction) of the chamber 200 in order to prevent the blood sample from scattering by a centrifugal force. The micro fluid passage 201 functioning as an air port has to be connected to the chamber 200 in a site 200*a* on the side opposite that of the injection port 204, that is, on the outer peripheral side. However, if blood plasma 205 and blood cells 206 are separated by a centrifugal force, then blood cells 206 contained in an amount of approximately 40-50% in the blood sample remain in the site 200*a* on the outermost peripheral side of the chamber 200*a* and the open section of the micro fluid passage 201 leading to the chamber 200 is clogged, thereby making the delivery impossible. If the connection position of the micro fluid passage 201 to the microchamber 200 is set from the inner periphery, as shown in FIG. 22, in order to avoid this clogging with the blood cells 206, then the air present in the microchamber 200 cannot be completely drained from the micro fluid passage 201 when the blood sample is introduced from the injection port 204, air bubbles 208 remain in the site 200*a* located on the outermost peripheral side of the microchamber 200, and air bite occurs, and metered introduction of the blood sample becomes impossible.

For the reasons described above, an air port has to be provided on the side of the chamber that is opposite the injection port, separately from the micro fluid passage, in order to drain reliably the air present in the chamber and to introduce metered quantities of the blood sample. However, in a structure where openings are provided at both ends of the chamber, that is when an injection port and air port are provided, the blood sample is scattered from one of the openings by a centrifugal force. As a result, an operation of sealing at least any one of the openings after the blood sample has been introduced is required. For example, an operation of pasting a sheet piece having adhesive capability surpassing the centrifugal force is required.

SUMMARY OF THE INVENTION

It is an object of the present invention to provide a blood processing apparatus and a blood introducing method making it possible to introduce a metered quantity of a blood sample into a chamber and conduct manipulations of the blood without the operation for closing the opening communicated with the chamber after the blood sample has been introduced.

A first aspect of the present invention provides a blood processing apparatus comprising a platform, a first chamber formed inside the platform, an injection port formed in the platform, communicating the first chamber with an outside of the platform, and adapted to introduce a blood sample into the first chamber, an air port formed in the platform and communicating the first chamber with the outside of the platform, and a blood coagulant held on a port wall surface of the air port and/or around a portion of a surface of the platform where the air port is opened.

When the blood sample is introduced from the injection port, the blood sample can be introduced into the first chamber, while exhausting the air in the first chamber through the air port. Therefore, the blood sample can be introduced into the entire first chamber, without residual air in the first chamber. As a result, the metered quantity of the blood sample can be introduced into the first chamber. For this characteristic, the blood processing apparatus of the first invention is suitable for a process such as measurement and analysis that requires quantitative accuracy.

The blood coagulant reacts with the blood sample introduced into the first chamber and causes coagulation of the blood sample. The air port is sealed by the coagulated blood sample. Therefore, after the blood sample has been introduced into the first chamber, the blood sample is prevented from scattering to the outside of the platform through the air port even if a process where a centrifugal force acts upon the blood sample in the first chamber, such as a centrifugal separation of blood cells and blood plasma or a delivery of the blood sample, is conducted. Further, no special operation, such as attaching a sheet piece for sealing the air port, is necessary.

The diameter of the air port is preferably 10 µm or more to 3 mm or less. Setting the diameter of the air port within this range assures reliable exhaustion of the air in the first chamber to the outside of the platform when the blood sample is introduced. Further, the air port can be reliably sealed by coagulated blood platelets contained in the blood, thereby preventing the blood sample from scattering from the air port under the effect of a centrifugal force acting during centrifugal separation of blood cells and blood plasma or during process such as delivery.

The blood coagulant comprises at least one substance for initiating coagulation of the blood sample or aggregation of blood platelets in the blood sample.

Specifically, the blood coagulant preferably comprises calcium ions or ionomycine of not less than 0.2 µmol and not more than 2 mmol. These substances can cause the initiation of the coagulation of the blood platelets in the blood, thereby sealing the air port.

More specifically, the blood coagulant preferably comprises at least one of tissue thromboplastin, partial thromboplastin, activated partial thromboplastin, and activated cephaloplastin. These substances enable rapid initiation of the coagulation of the blood platelets in the blood.

Further, the blood coagulant preferably comprises at least one of thrombin, epinephrine, a blood platelet activating factor, ristocetin, a thrombin receptor-sensitive peptide, and arachidonic acid. These substances also enable rapid initiation of the coagulation of the blood platelets in the blood.

The blood coagulant preferably has hydrophilic property. When the blood sample introduced into the first chamber comes into contact with the blood coagulant held around the air port, the port wall surface of the air port is rapidly wetted with the blood sample due to the capillary phenomenon. Therefore, the time required to seal the air port by coagulation of the blood sample after it has been introduced can be shortened.

The blood processing apparatus may further comprise a holding concave portion formed in the surface of the platform, a bottom wall of the holding concave portion being communicated with the air port and having an area larger than that of the air port, and the blood coagulant may be held at least around the air port on the bottom wall of the holding concave portion. Because a surface area of the blood coagulant is increased, a contact area of the blood coagulant and blood sample is increased. As a result, blood platelet coagulation in blood occurs more rapidly and the air port is more tightly sealed with the coagulated blood. Therefore, the time required to seal the air port by coagulation after the blood sample has been introduced into the first chamber can be shortened. Further, the blood sample located in the first chamber can be more reliably prevented from being scattered to the outside of the platform through the air port during blood processing such as centrifugal separation. The area of the bottom wall of the holding concave portion is preferably not less than 0.015 mm$^2$ and not more than 30 mm$^2$.

It is preferred that the platform is capable of rotating around a central axis of rotation, that the blood processing apparatus further comprises a rotary drive unit capable of rotatably driving the platform around the central axis of rotation, that the injection port is formed in a site of the first chamber on a side of the central axis of rotation, and that the air port is formed in a site of the first chamber farther from the central axis of rotation than the injection port. Disposing the air port in a position farther from the central axis of rotation than the injection port can reliably prevent the residual air during introduction of the blood sample from the injection port into the first chamber. Further, when the platform is rotatably driven by the rotary drive unit, sealing the air port with the blood coagulated with the blood coagulant can reliably prevent the blood sample from scattering to the outside of the platform by the centrifugal force.

The blood processing apparatus may further comprise a second chamber formed inside the platform, and a fluid passage formed inside the platform and communicating the first chamber with the second chamber, and a fluid passage end portion of the fluid passage connected to the first chamber may be disposed closer to the central axis of rotation of the platform than the air port.

Because the fluid passage communicating the first chamber with the second chamber is connected to the first chamber at a position closer to the rotation center than the air port, the fluid passage end portion can be kept in an open status, without being clogged with blood cells, even when blood cell-blood plasma separation is executed by rotating the platform around the central axis of rotation with the rotary drive unit. Therefore, blood plasma can be delivered from the first chamber into the second chamber via the fluid passage after the blood cell-blood plasma separation.

It is preferred that the fluid passage end portion of the fluid passage connected to the first chamber extends in a rotation direction of the platform, and holds the liquid sample in the first chamber by a capillary force, and that the rotary drive unit is capable of rotatably driving the platform around the central axis of rotation so that an inertial force exceeding the capillary force acts upon the blood sample in the fluid passage end portion.

In this context, the rotation direction is defined as a direction perpendicular to a virtual line perpendicular to the central axis of rotation and located in the same plane with the virtual line. For example, when the platform is secured to a rotary shaft, the tangential direction perpendicular to the radial direction of the rotary shaft is a rotation direction. The rotation direction may be a clockwise direction or a counterclockwise direction with respect to the central axis of rotation in the plan view.

The blood sample injected from the injection port and then accommodated in the first chamber is held in the fluid passage end portion by a capillary force. When the platform is rotated by the platform rotary unit, an inertial force acts in the rotation direction on the blood sample held in the fluid passage end portion. When this inertial force exceeds the capillary force, the blood sample located in the first chamber flows into the fluid passage and is delivered into the second chamber.

Detection electrode for analyzing a blood component in the second chamber may also be provided.

After the introduction of the blood sample into the first chamber and the centrifugal separation of blood cells and blood plasma, only the blood plasma component can be delivered into the second chamber via the fluid passage and then electrochemically analyzed with the detection electrodes in the second chamber. For example, if a buffer component for measurement, an enzyme for detection, and an electron acceptor are held in the second chamber, then the blood plasma component delivered into the second chamber will react with those substances. This enables estimation on the amount of components contained in the blood from an electric current value measured with the detection electrode. Therefore, information necessary for predicting the disease and evaluating the health state can be obtained.

For example, the platform comprises a first platform having the injection port and the air port formed therein so as to pass through in the thickness direction, and a second platform joined to the first platform and having the first chamber, the second chamber, and the fluid passage formed therein.

In this arrangement, it is not necessary to form integrally the first chamber with the injection port and air port. Further, concave portions of adequate shapes formed in the second platform can function as the first chamber, second chamber, and fluid passage. Furthermore, through holes formed in the first platform can function as the injection port and air port. Therefore, the platform can be efficiently manufactured and the production cost of the blood processing apparatus can be reduced.

The platform structure in which the first and second platforms are joined together can realize a more complex fluid passage structure. For example, the detection electrode can be provided inside the second chamber by employing a film deposition technique such as vapor deposition or sputtering on a joining side surface of the first platform.

The first platform having the air port provided therein is a body separated from the second platform provided with the first chamber. Therefore, the blood coagulant can be held locally and easily only in the necessary locations by dropping a solution containing the blood coagulant onto the necessary locations such as the port wall surface of the air port of the first platform, around the air port, and on bottom wall of the holding concave portion.

It is preferred that a plurality of fluid passage sites comprising the first chamber, the second chamber, and the fluid passage formed in the platform. By this arrangement, the operations such as centrifugal separation, delivery, and component analysis can be executed simultaneously and in parallel with respect to blood samples in a plurality of first chambers provided in one platform. Therefore, the efficiency of those operations can be increased. Moreover, integrally providing a plurality of fluid passage sites in one platform enables reduction of the production cost.

A second aspect of the present invention provides a method for introducing a blood sample into a chamber having an injection port, an air port, and a blood coagulant held on a periphery of the air port. The method comprising, introducing blood from the injection port into the chamber so as to cause exhaustion of air in the chamber to an outside of the chamber via the air port, and bringing the blood sample that have introduced to the chamber into contact with the blood coagulant so as to seal the air port with the blood sample coagulated by the blood coagulant.

When the blood sample is introduced from the injection port into the chamber, the air present inside the chamber is exhausted through the air port. Therefore, the blood sample can be introduced into the entire chamber, without the residual air the chamber. As a result, the metered quantity of the blood sample can be introduced into the chamber. The blood sample introduced into the chamber comes into contact with the blood coagulant and is coagulated, thereby sealing the air port. Therefore, after the blood sample has been introduced into the chamber, the blood sample is prevented from scattering through the air port even if a process where a centrifugal force acts upon the blood sample in the first chamber, such as a centrifugal separation of blood cells and blood plasma or a delivery of the blood sample, is conducted. Furthermore, no special operation such as pasting a sheet piece for sealing the air port is necessary.

A fourth aspect of the present invention provides a method for holding the blood coagulant in the chamber of the above-described blood processing apparatus. The method comprising, preparing a solution in which the blood coagulant is dissolved at a predetermined concentration, dropping the solution on the port wall surface and/or around the portion of the surface of the platform where the air port is open, and drying the dropped solution.

The dropped solution is preferably dried by lyophilization. Even if the blood coagulant is unstable at a temperature higher than room temperature, the blood coagulant can be held in the chamber with good stability.

With the blood processing apparatus in accordance with the present invention, providing an air port makes it possible to introduce a blood sample into the entire chamber, without causing air bites. As a result, the quantity of the blood sample introduced into the chamber can be the same in each cycle. Therefore, the apparatus is suitable for measurements requiring quantitative accuracy. In other words, the quantity of components contained in blood can be determined quantitatively with high accuracy and good reproducibility.

Furthermore, providing an air port increases the degree of freedom in arranging the fluid passage connected to the chamber. As a result, a more complex liquid delivery behavior can be realized by simple operations.

Furthermore, because the air port is sealed by solidifying the blood sample introduced into the chamber by contact with a blood coagulant, the blood is not scattered from the opening, for example, even when the blood cells and blood plasma are centrifugally separated. Furthermore, blood processing can be conduced without carrying out a special operation such as pasting a sheet piece to seal the air port. As a result, the time required for treating the blood, e.g. for analysis, can be shortened. Furthermore, the operations are conducted in an automated mode in a simple manner, and safety of the operator can be ensured when blood, which can be contagious, is handled.

BRIEF DESCRIPTION OF THE DRAWINGS

Other objects and characteristics of the present invention shall be clarified by the following description on the preferred embodiments with reference to the accompanying drawings.

FIG. 4 is an exploded perspective view of the rotatable platform of the first embodiment of the present invention;

FIG. 11 is an exploded perspective view illustrating a first alternative of the rotatable platform;

DESCRIPTION OF THE PREFERRED EMBODIMENTS

Figure 1:
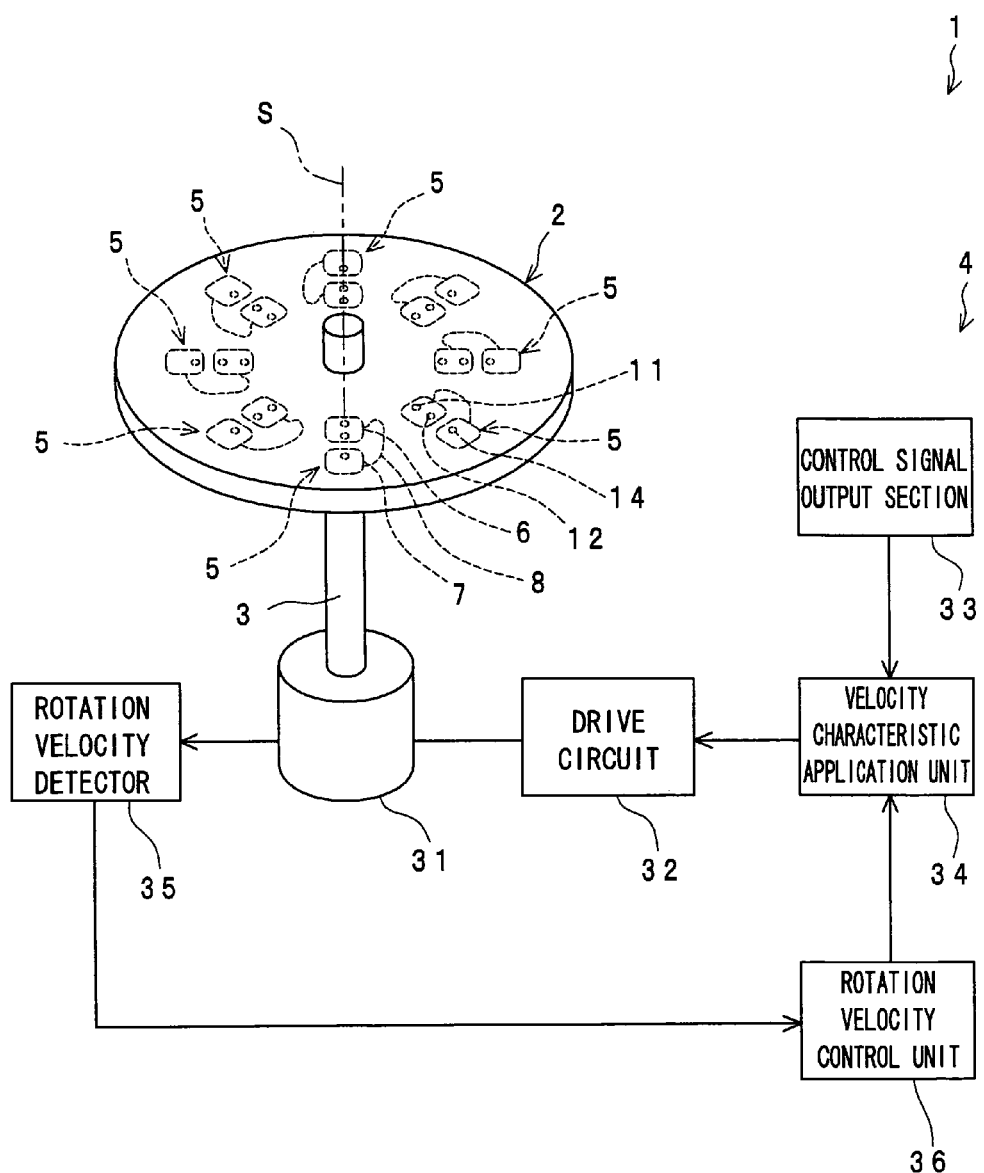
FIG. 1 is a schematic structural view illustrating the blood analysis apparatus of a first embodiment of the present invention.

The embodiments of the present invention will be described below in greater detail with reference to the appended drawings.

First Embodiment

A blood processing apparatus 1 of a first embodiment of the present invention is shown in FIG. 1 to FIG. 4.

This liquid delivery apparatus 1 comprises a rotatable platform 2, a rotary shaft 3 having the rotatable platform 2 fixed thereto, and a rotary drive unit 4 for rotary driving the rotary shaft 3. The rotary shaft 3 is disposed in a posture such that the axial line thereof (central line of rotation) S extends in the vertical direction, and the rotatable platform 2 is fixed to the upper end side thereof. The rotatable platform 2 is round in a plan view thereof, and the center of the rotatable platform 2 coincides with the central line S of rotation. On the other hand, the below-described motor 31 is connected to the lower end side of the rotary shaft 3.

The rotatable platform 2 rotates together with the rotary shaft 3. In the explanation hereinbelow, the rotation direction of the rotary shaft 3 is defined as a direction perpendicular to the radial direction r of the rotary shaft 3, as shown by arrows R1, R2 in FIG. 2. In other words, the rotation direction is defined as a direction perpendicular to a virtual line that is perpendicular to the axial line S of the rotary shaft 3 and located on the same plate as this virtual line. The rotatable platform 2 can be rotated in two directions, that is, in a clockwise direction R1 and counterclockwise direction R2, in the plan view thereof.

Figure 2:
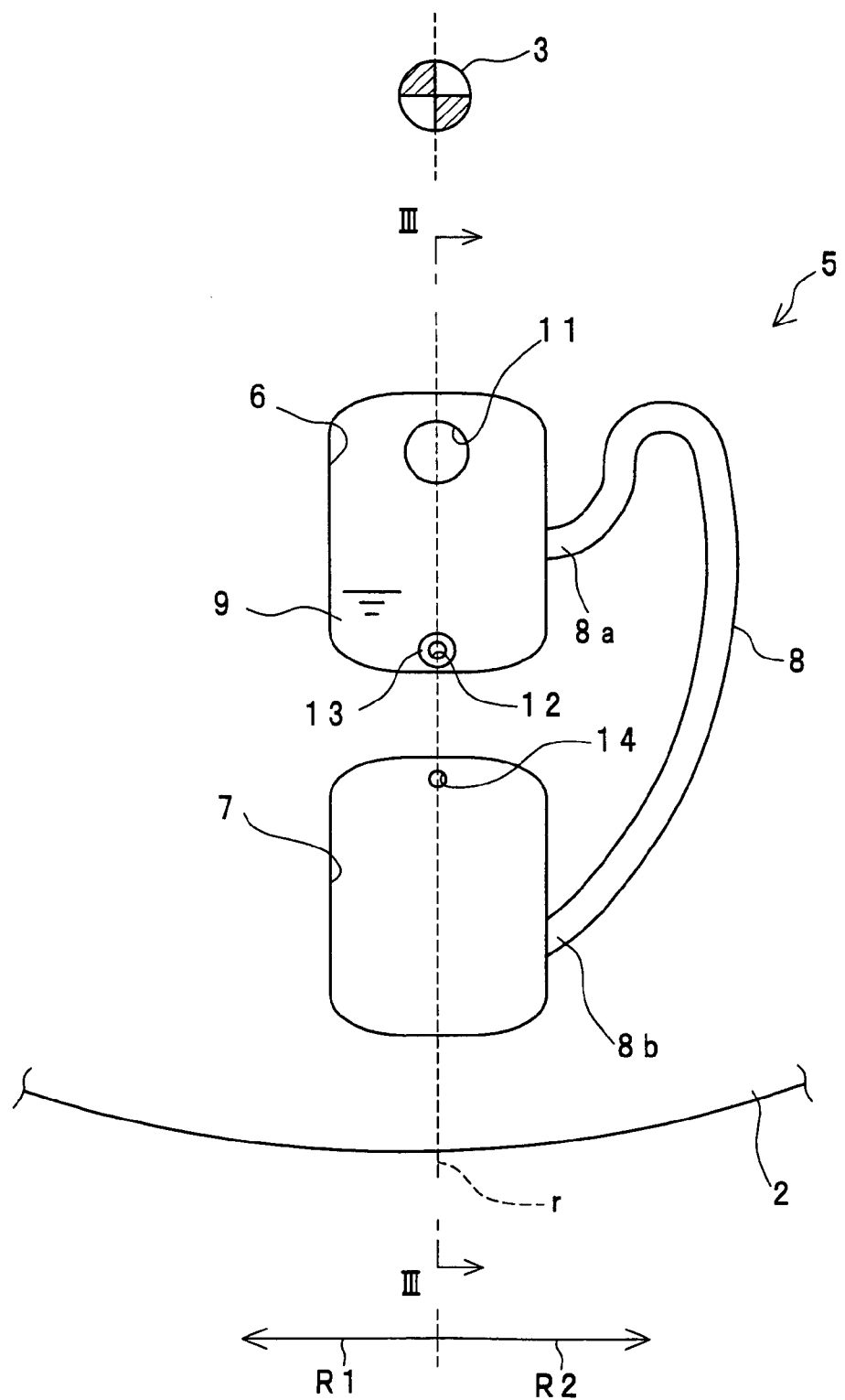
FIG. 2 is a partially enlarged plan view of the rotatable platform of the blood analysis apparatus of the first embodiment of the present invention.

As shown in FIG. 1, in the rotatable platform 2, a plurality of fluid passage sites 5 are arranged radially around the rotary shaft 3. Referring to FIG. 2 together with FIG. 3A and FIG. 3B, the fluid passage site 5 comprises an introducing chamber (first chamber) 6 into which a blood sample is to be introduced, a downstream chamber (second chamber) 7 into which the blood sample is delivered from the introducing chamber 6, and a micro fluid passage 8 for fluidly connecting the introducing chamber 6 with the downstream chamber 7. Providing a plurality of fluid passage sites 5 integrally in one rotatable platform 2 makes it possible to execute in parallel the below-described operations with respect to a plurality of blood samples, thereby increasing the efficiency of the operations. Furthermore, forming a plurality of fluid passage sites 5 in one rotatable platform 2 reduces the production cost.

The introducing chamber 6 is formed inside the rotatable platform 2 and spatially confined. However, an injection port 11 with a circular cross section that passes from the upper wall of the introducing chamber 6 to the surface 2a of the rotatable platform 2 and links the inside of the introducing chamber 6 with the outside of the rotatable platform 2 is formed in the rotatable platform 2. The injection port 11 is used to inject the blood sample 9 into the introducing chamber 6. Furthermore, an air port 12 with a circular cross section that passes from the upper wall of the introducing chamber 6 to the surface 2a of the rotatable platform 2 and links the inside of the introducing chamber 6 with the outside of the rotatable platform 2 is also formed in the rotatable platform 2. An inlet end section 8a of the fluid passage 8 is connected to the introducing chamber 6. The dimensions and volume of the introducing chamber 6 have to be determined according to the amount of blood sample 9 and it is preferred that the volume be 0.1 μL or more to 100 μL or less.

Referring to FIG. 2, the introducing chamber 6 has an almost rectangular shape in the plan view thereof. The injection port 11 is disposed close to the side wall of the introducing chamber 6 on the side of the rotary shaft 3. Furthermore, the surface area of the injection port 11 in the plan view thereof is set to be sufficiently small by comparison with the surface area of the introducing chamber 6 in the plan view thereof. Because the position and surface area of the injection port 11 are thus set, the blood sample 9 flows from the injection port 11 into the fluid passage 8, without leak or scattering, under the effect of an outward centrifugal force acting in the radial direction r during the rotation of the rotatable platform 2. On the other hand, the air port 12 is disposed close to the side wall of the introducing chamber 6 that is the farthest from the rotary shaft 3. In other words, the air port 12 is disposed in a site farther from the rotary shaft 3 than the injection port 11. Furthermore, in the plan view of the introducing chamber 6, the entry end section 8a of the fluid passage 8 is open at the side wall on the right site. The entry end section 8a is disposed on the rotary shaft 3 side from the air port 12. Therefore, the injection port 11, entry end section 8a of the fluid passage 8, and air port 12 are disposed sequentially outwardly in the radial direction of the rotary shaft 3.

Figure 3:
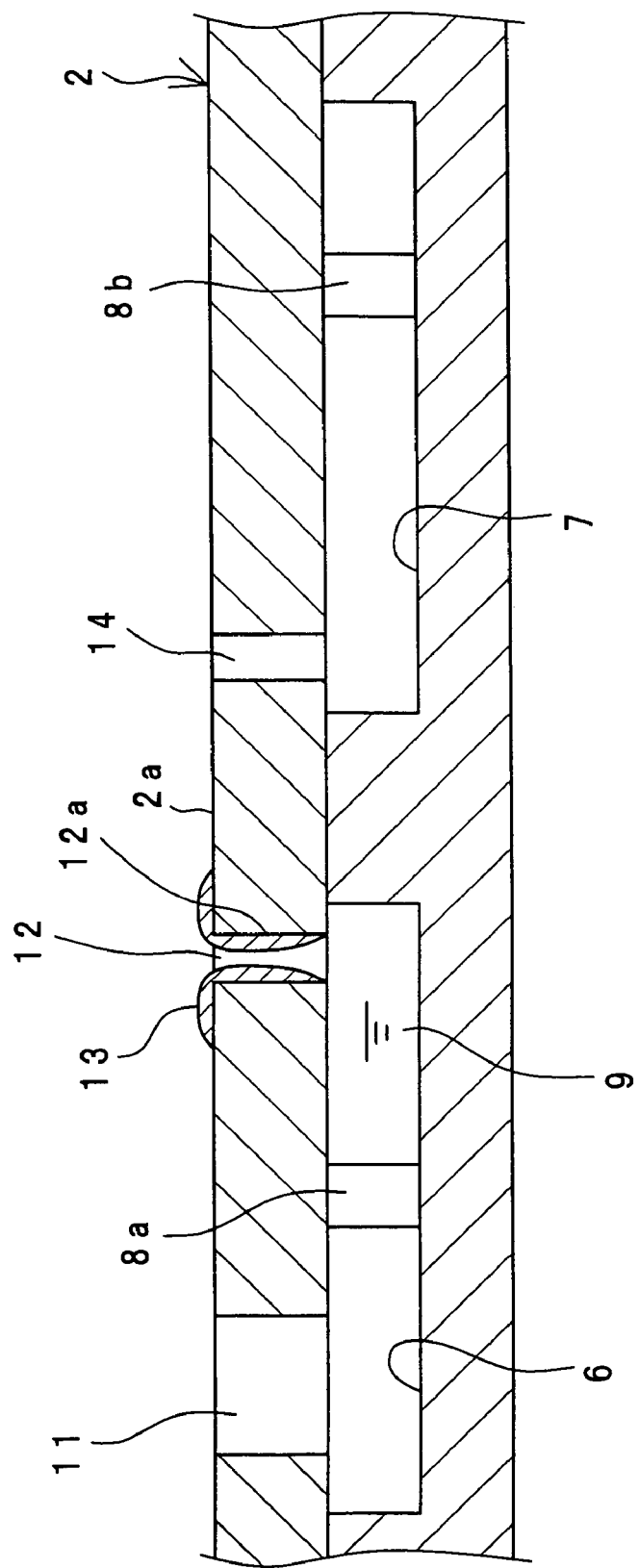
FIG. 3 is a partial cross section along the III-III line in FIG. 2.
Figure 5A:
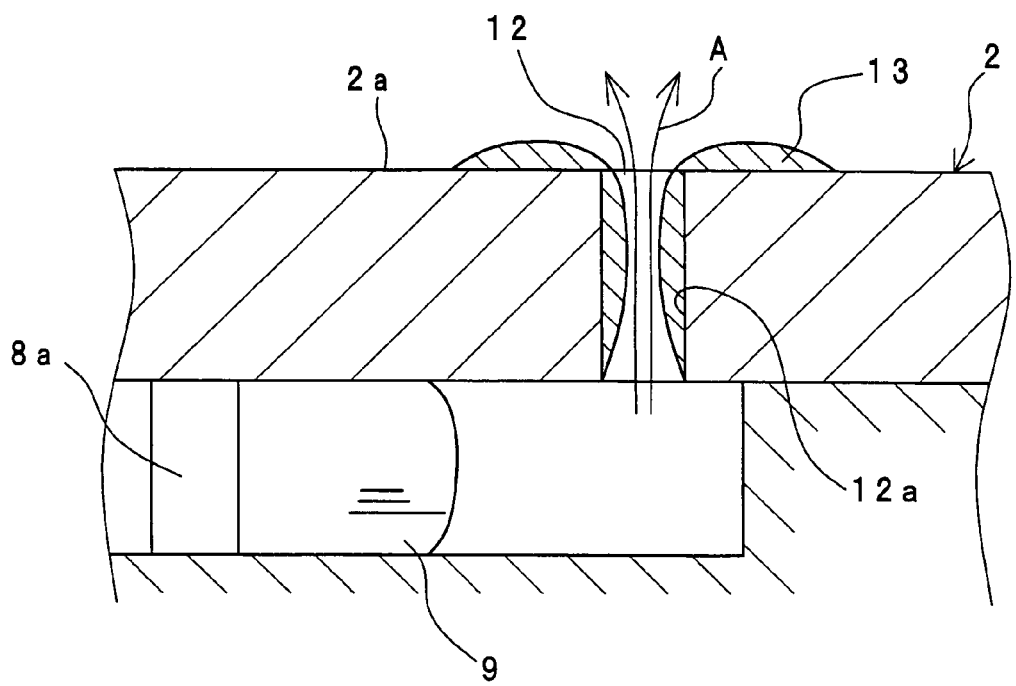
FIG. 5A is a partially enlarged plan view of the rotatable platform illustrating the state where the air present in the supply chamber is drained from the air port.

As shown in FIG. 3 and FIG. 5A, the blood coagulant 13 is held on the port wall surface 12a of the air port 12 and around the portion of the surface 2a of the rotatable platform 2 where the air port 12 is open. As described below in greater detail, the blood coagulant 13 has a function of causing solidification of the blood sample 9 introduced into the introducing chamber 6 and sealing the air port 12 with the solidified blood sample. The blood coagulant 13 may be also held on any one of the port wall surface 12a of the air port 12 and around the portion of the surface 2a of the rotatable platform 2 where the air port 12 is open.

The blood coagulant 13 can coagulate blood and comprises calcium ions and ionomycine. The content ratio of calcium ions or ionomycine in the blood coagulant 13 is preferably 0.2 μmol or more to 2 μmol or less. In the blood coagulation process, calcium ions are responsible for transferring information inside the cells of blood platelets. Therefore, if calcium ions can be caused to be present in an excess amount inside the cells, the blood coagulates rapidly. Furthermore, because ionomycine is a calcium ion chelator having cell membrane permeability, the blood is coagulated more efficiently.

The blood coagulant 13 may contain other substances. Those substances may be generally classified into substances activating calcium stores present inside the blood platelets and substances activating endogenous or exogenous paths of prothrombin conversion. Blood coagulants activating endogenous or exogenous paths of prothrombin conversion include tissue thromboplastin, partial thromboplastin, activated partial thromboplastin, and activated cephaloplastin. Furthermore, coagulation of blood platelets in blood can be rapidly initiated if the blood coagulant 13 comprises thrombin, epinephrine, a blood platelet activating factor (RAF), ristocetin, a thrombin receptor-sensitive peptide (TRAP), and arachidonic acid. Furthermore, blood coagulants 13 well known to those skilled in the art, for example, such as disclosed in Japanese Patent Application Tokuhyo No. H9-504614, can be employed as the blood coagulant.

Furthermore, the blood coagulant 13 preferably has hydrophilic properties attained, for example, by including a substance imparting hydrophilic properties. If the blood sample 9 introduced into the introducing chamber 6 comes into contact with the blood coagulant 13 having hydrophilic properties, the port wall surface 12a of the air port 12 is rapidly wetted due to a capillary phenomenon. Therefore, the time required to seal the air port 12 by coagulation of the blood sample 9 after the blood sample 9 was introduced is shortened and a transition can be rapidly made to conducting operations with the blood sample 9.

The downstream chamber 7 is formed inside the rotatable platform 2 and spatially closed. However, an air port 14 with a round cross section that passes through from the upper wall of the downstream chamber 7 to the upper surface of the rotatable platform 2 and links the inside of the downstream chamber 7 with the outside of the rotatable platform 2 is formed in the rotatable platform 2. This air port 14 serves to drain the air present inside the downstream chamber 7 to the outside of the rotatable platform 2 when the blood sample 9 flows into the downstream chamber 7. Furthermore, an outlet end section 8b of the fluid passage 8 is connected to the downstream chamber 7. The air port 14 is located closer to the rotary shaft 3 than the outlet end section 8b in order to prevent the blood sample 9 located inside the downstream chamber 7 from scattering under the effect of a centrifugal force acting when the rotatable platform 2 is rotated. The dimensions and volume of the downstream chamber 7 have to be determined according to the amount of liquid in the blood sample 9, and it is preferred that the volume thereof is 0.1 μmol or more to 100 μmol or less.

The fluid passage 8 is formed inside the rotary platform 2 and spatially closed. The fluid passage 8 has to be a fine fluid passage so that the blood sample 9 can be reliably delivered from the introducing chamber 6 to the downstream chamber 7 through the fluid passage 8. More specifically, the volume of the fluid passage 8 is preferably equal to or less than that of the introducing chamber 6 and downstream chamber 7. The width of the fluid passage 8 is preferably 1 μm or more to approximately 2000 μm or less, and the depth of the fluid passage 8 is preferably 1 μm or more to approximately 2000 μm or less. It is further preferred that the fluid passage 8 have a fluid passage width of 50 μm or more to approximately 500 μm or less and a fluid passage depth of 10 μm or more to approximately 100 μm or less. It is also preferred that the width and depth of the fluid passage 8 be less than those of the introducing chamber 6 and downstream chamber 7.

The inlet end section 8a of the fluid passage 8 connected to the introducing chamber 6 functions as a valve for removably holding the blood sample 9 that has been accumulated in the introducing chamber 6. The inlet end section 8a extends in the counterclockwise direction R1 of the two rotation directions of the rotatable platform 2 from the introducing chamber 6.

Wetting ability of the wall surfaces constituting the fluid passage site 5 will be described below. The fluid passage wall of the inlet end section 8a of the fluid passage 8 is composed of a hydrophobic material or subjected to a treatment providing it with hydrophobic properties. If the inlet end section 8a has hydrophobic properties, the liquid that has been accumulated in the introducing chamber 6 can be reliably held in the inlet end section 8a by a capillary force. On the other hand, the remaining portions of the fluid passage site 5, that is the wall surface of the introducing chamber 6, the wall surface of the downstream chamber 7, and the wall surface of the entire fluid passage 8 (including the outlet end section 8b), excluding the inlet end section 8a, are composed of a hydrophilic material or subjected to a treatment providing them with hydrophilic properties. If those portions have hydrophilic properties, then the liquid that flowed from the introducing chamber 6 into the fluid passage 8 will reliably flow into the downstream chamber 7 by the wetting effect and capillary tube phenomenon.

Examples of hydrophobic materials include semiconductor materials such as single-crystal silicon, amorphous silicon, silicon carbide, silicon oxide, and silicon nitride, inorganic insulating materials selected from the group including alumina, sapphire, forsterite, silicon carbide, silicon oxide, and silicon nitride, and organic materials selected from the group including polyethylene, ethylene, polypropylene, polyisobutylene, polyethylene terephthalate (PET), unsaturated polyesters, fluorine resins, polyvinyl chloride, polyvinylidene chloride, polyvinyl acetate, polyvinyl alcohol, polyvinyl acetals, acrylic resins, polyacrylonitrile, polystyrene, acetal resins, polycarbonates (PC), polyamides, phenolic resins, urea resins, epoxy resins, melamine resins, styrene-acrylonitrile copolymer, acrylonitrile-butadiene styrene copolymer, silicone resins, polyphenylene oxide, and polysulfones. The preferred among those materials are PET and PC. Examples of materials that can provide hydrophobic properties include fluorine resin coating agents and silicone coating agents. The preferred among them are fluorine resin coating agents.

Examples of hydrophilic materials include glass, quartz glass and metal materials such as aluminum, copper, and stainless steel. The metal materials have to have a clean surface obtained by removing organic substances that adhered thereto. Examples of materials that can provide hydrophilic properties include surfactants such as Triton X and polymer compounds having hydrophilic groups such as hydroxyl groups, sulfone group, and carboxyl groups. It is preferred that surfactants be used.

Referring to FIG. 3 and FIG. 4, the rotatable platform 2 of the present embodiment has a two-layer structure in which an upper substrate 21 comprising the injection port 11 and air ports 12, 14 and a substrate 22 comprising the introducing chamber 6, downstream chamber 7, and fluid passage 8 are bonded in a laminated state thereof. A variety of methods known to those skilled in the art can be employed for joining the upper platform 21 and lower platform 22. For example, an adhesive material or a sheet having adhesive properties may be introduced between the platforms, or the platforms may be joined by ultrasound joining, thermal fusion joining, laminator processing, or other methods. A variety of methods known to those skilled in the art can be also used for forming the chambers and fluid passages. Examples of suitable methods include photolithography employed in fine processing of semiconductors, injection molding employed in plastic molding, machining, and transfer processing by producing a copy from a master substrate. Photolithography is the especially preferred method.

An example of the method for fabricating the rotatable platform 2 will be described below. This fabrication process comprises a step of coating a photoresist on the lower platform 22 and forming the fluid passage 8 by lithography, a step of forming the introducing chamber 6 and downstream chamber 7, a step of forming fluid inlet and outlet ports (the injection port 11 and air ports 12, 14) in the upper platform 21, and a step of sealing the upper part of the fluid passage site 5 with the upper platform 21 by joining the upper platform 21 with the lower platform 22. The process will be successively explained below starting from the step of forming the fluid passage 8.

First, a negative thick-film photoresist is coated on a glass substrate subjected to washing. Here, a photoresist appropriate for the size of the fluid passage is selected. For example, KMPR1030 (manufactured by Kayaku Microchem Corp.) is an excellent choice from the standpoint of aspect ratio and suitability for forming thick films. A rotation coating system such as a spin coater can be used. When KMPR1030 is rotation coated with a spin coater, pre-rotation is conducted for 10 sec at 500 rpm and main rotation is conducted for 30 sec at 1000 rpm. The film thickness can be changed by changing the rotation speed of the main rotation. For example, a thickness of 57 μm and 48 μm can be obtained at a rotation speed of the main rotation of 1000 rpm and 1070 rpm, respectively. Then, pre-baking is conducted for 20 min at a temperature of 95° C. and a mask having a fluid passage 8 and chambers 6, 7 drawn thereby is exposed. The exposure intensity and exposure time are assumed to be appropriately corrected by the film thickness. For example, it is desired that the exposure intensity be approximately 1700 mJ/cm$^2$. Then, PEB (Post Exposure Bake) is conducted for 6 min at a temperature of 95° C., development is conducted, and the pattern of the fluid passage 8 and chambers 6, 7 is formed by photolithography. The sites of chambers 6, 7 of the lower platform 22 are then formed by cutting. Finally, the upper platform 21 having the injection port 11 and air ports 12, 14 opened therein is pasted onto the lower platform 22.

The blood coagulant 13 has to be held on the port wall surface 12a of the air port 12 and around a portion of the surface 2a of the rotatable platform 2 where the air port 12 is open, before the upper platform 21 is joined to the lower platform 22. The below-described dry holding method is used for holding the blood coagulant 13.

The dry holding method comprises the steps of producing a solution in which the blood coagulant 13 is dissolved to the preset concentration, dropping the solution on the port wall surface 12a and around a portion of the surface 2a of the rotatable platform 2 where the air port 12 is open, and drying the dropped solution. The step of drying the solution comprising the blood coagulant 13 may be carried out by lyophilization. Conducting lyophilization makes it possible to hold the blood coagulant 13 with good stability even when the blood coagulant 13 is unstable at a temperature above the room temperature.

The above-described laminated structure of the rotatable platform 2 can be important for holding the blood coagulant 13 only around the air port 12 by the dry holding method and preventing the blood coagulant 13 from adhering to the introducing chamber 6, downstream chamber 7, and fluid passage 8. Referring to FIG. 3 and FIG. 4, the introducing chamber 6, downstream chamber 7, and fluid passage 8 are not formed in the upper platform 21 where the air port 12 is formed. Therefore, the blood coagulant 13 can be held only around the air port 12 by dropping the solution of the blood coagulant 13 only on the site of the upper platform 21 where the air port 12 was formed, drying, and then joining the upper platform 21 and lower platform 22.

As an example, when the volume of the introducing chamber 6 is 30 μL and the diameter of the air port 12 is 1 mm, a total of 10 μL of a 25 mM CaCl$_2$ solution is dropped around the air port 12 and dried by allowing to stay as is for 6 h at normal temperature. Coagulation of blood with the blood coagulant 13 thus held was completed within 30 sec to 1 min 30 sec, and fibril precipitation occurred. Then, a 10-fold diluted tissue thromboplastin solution and a 10 mM CaCl$_2$ mixed solution was dropped in an amount of 10 μL and lyophilized. In this case, coagulation of blood was completed within 5 sec to 10 sec after the blood came into contact with the blood coagulant 13. When the introducing chamber 6 was maintained at a temperature of 37° C. and blood was similarly introduced, the coagulation time was approximately 2 sec. With the commercial partial thromboplastin and activated partial thromboplastin, coagulation of blood in the area of the air port 12 was completed within 30 sec and 50 sec, respectively.

Figure 7:
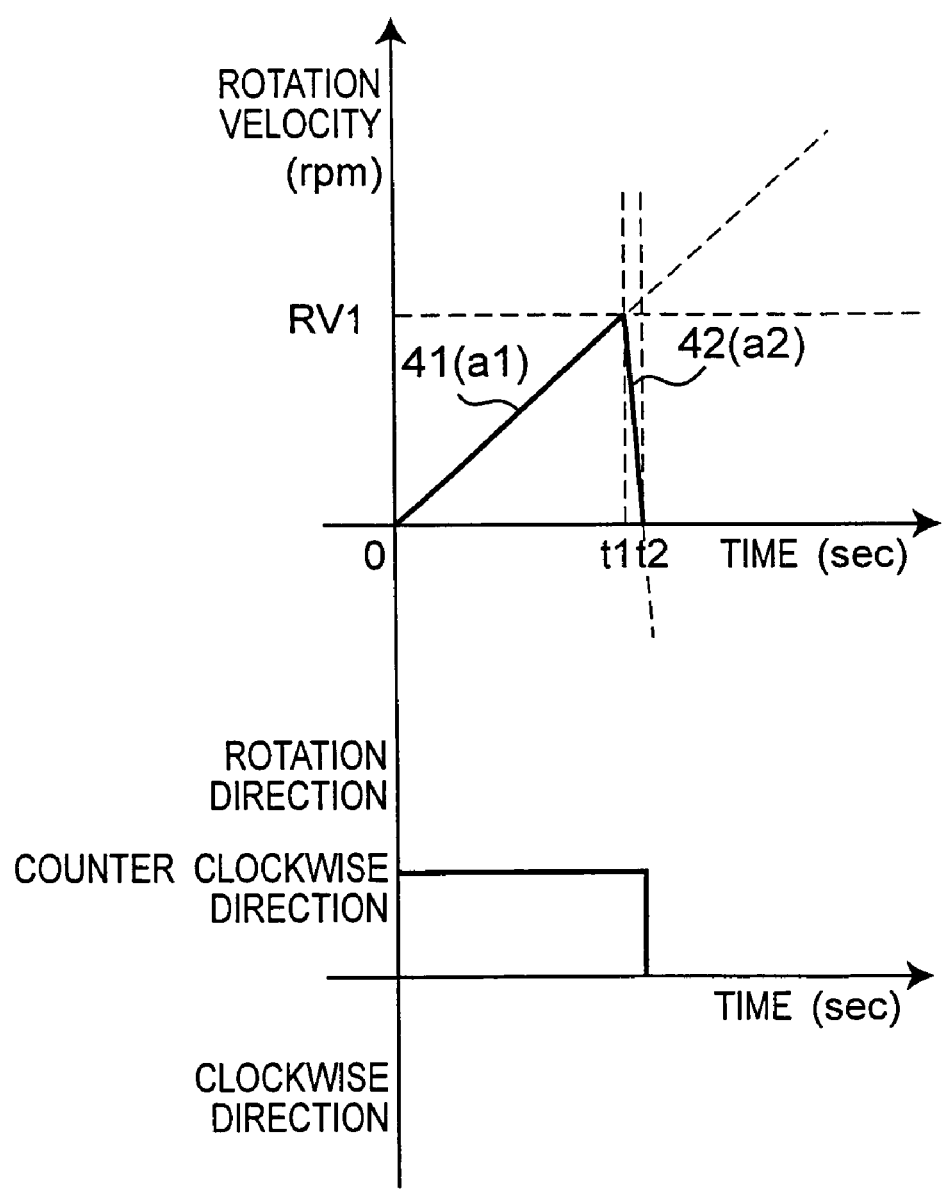
FIG. 7 is a diagram illustrating the velocity waveform and rotation direction of a first example of delivery operation of the blood analysis apparatus of the first embodiment of the present invention.

The rotary drive unit 4 will be explained below with reference to FIG. 1. The rotary drive unit 4 comprises a motor 31 mechanically connected to the rotary shaft 3 and serving to rotate the rotary shaft 3 and the rotatable platform 2 fixed to the rotary shaft 3 and a drive circuit 32 of the motor 31. Furthermore, the rotary drive unit 4 comprises a control signal output unit 33 for outputting a control signal and a velocity characteristic application unit 34 for providing the desired velocity characteristic, for example such as shown in FIG. 7, to the drive circuit 32 of the motor 31, based on the control signal inputted from the control signal output unit 33. The control signal output unit 33 may be an external computer separate from the liquid delivery apparatus 1.

A DC motor, a DC brushless motor, an AC motor, or a stepping motor can be used for the motor 31. The stepping motor is preferred because rapid rotation and abrupt braking of the rotatable platform 2 can be easily realized by applying an external drive signal. Furthermore, The DC motor does not require a special drive circuit 32. When a DC brushless motor is employed as the motor 31, if the drive circuit 32 has a function of applying a reverse rotation voltage, then even faster braking can be realized.

Furthermore, the rotary drive unit 4 comprises a rotation velocity detector 35 for detecting the rotation velocity of the rotatable platform 2 during rotation and a rotation velocity control unit 36 for correcting the velocity characteristic application unit 34. The actual rotation velocity of the rotatable platform 2 detected with the rotation velocity detector 36 is sent to the rotation speed control unit 36. The rotation velocity control unit 36 corrects the velocity characteristic provided by the velocity characteristic application unit 34 if there is a difference between the actual detected rotation speed and the velocity characteristic that has to be provided to the motor 31 by the velocity characteristic application unit 34. Driving the rotatable platform 2 in this manner, while feedback returning the actual rotation velocity of the rotatable platform 2 and correcting the velocity characteristic makes it possible to realize the stable liquid delivery and to improve cyclic reproducibility of the liquid delivery.

An example of the operation of the blood processing apparatus 1 of the present embodiment will be explained below.

Figure 22:
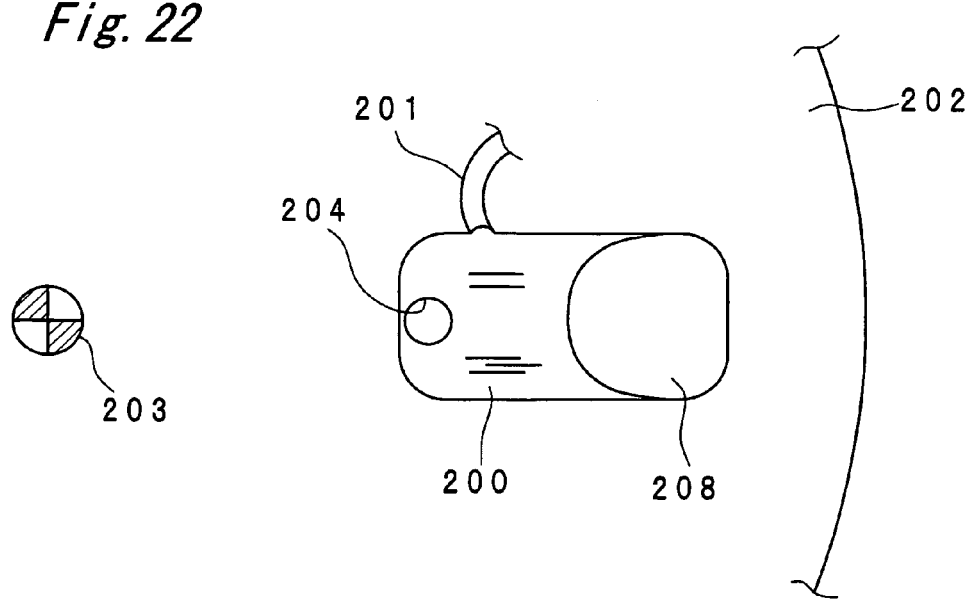
FIG. 22 is a schematic drawing for explaining the problems arising when a micro fluid passage is connected to the chamber on the rotary shaft side.

First, a blood sample 9 is introduced into the introducing chamber 6. The blood sample 9 is introduced into the introducing chamber 6 from the injection port 11. As shown by arrow A in FIG. 5A, as the volume of the blood sample 9 inside the introducing chamber 6 increases, the air present in the introducing chamber 6 is drained to the outside of the rotatable platform 2 via the air port 12. As described hereinabove, the air port 12 is disposed close to the side wall of the introducing chamber 6 that is at the farthest side from the rotary shaft 3. Therefore, the blood sample 9 can be introduced into the entire introducing chamber 6, without leaving air bubbles (see reference numeral 208 in FIG. 22) and without the occurrence of air bites. As a result, constant amounts of blood sample 9 can be reliably introduced into the introducing chamber 6. In this respect, the blood processing apparatus 1 of the present embodiment is suitable for measurements and analysis requiring quantitative accuracy.

Figure 5B:
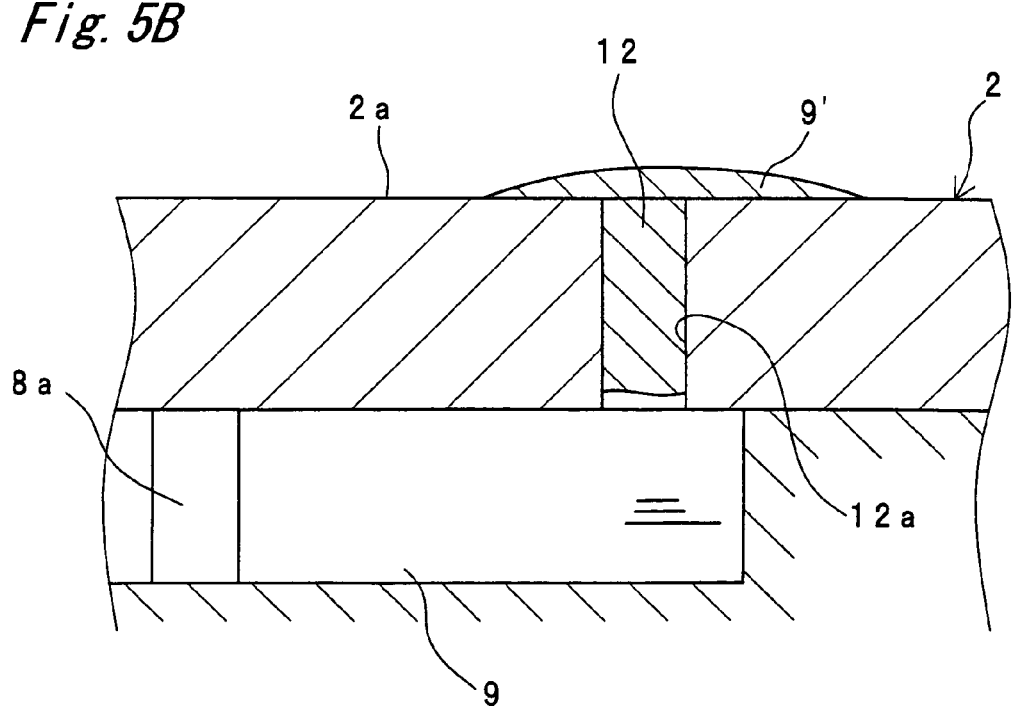
FIG. 5B is a partially enlarged plan view of the rotatable platform illustrating the state where the air is sealed by the coagulated blood.

If the blood sample 9 that was introduced into the introducing chamber 6 comes into contact with the blood coagulant 13, the blood coagulant 13 reacts therewith, as described hereinabove, and the blood sample 9 is coagulated. As a result, the air port 12 is sealed with the coagulated blood sample 9', as shown in FIG. 5B.

Figure 6:
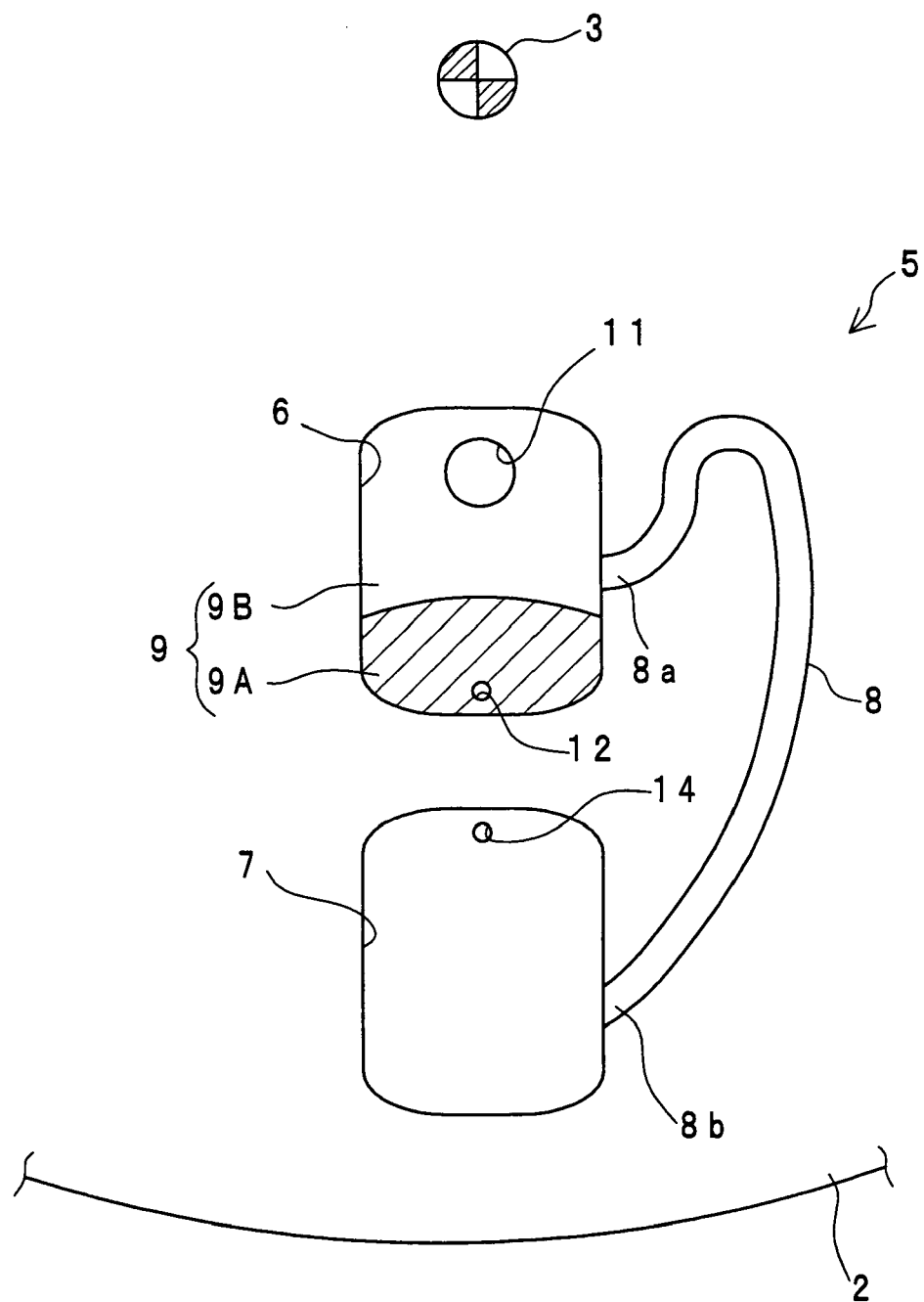
FIG. 6 is a partially enlarged plan view of the rotatable platform illustrating the state after blood cell-blood plasma separation.

After the air port 12 of the introducing chamber 6 has been sealed, a variety of operations can be conducted with respect to the blood sample 9. For example, the rotary drive unit 4 rotates the rotatable platform 2 in the clockwise direction R1 or counterclockwise direction R2 at the prescribed velocity, thereby centrifugally separating the blood sample 9 into blood cells 9A, which are a particulate component, and blood plasma 9B, which is a liquid component, as shown in FIG. 6. As described above, the inlet end section 8a of the fluid passage 8 is connected to the introducing chamber 6 in a site between the injection port 11 and air port 12 in the radial direction, rather than in the site of the introducing chamber 6 on the outside in the radial direction of the rotary shaft 3. Therefore, the inlet end section 8a of the fluid passage 8 maintains the open state, without being clogged by the blood cells 9A remaining in the site on the outside of the introducing chamber 6 due to centrifugal separation.

The blood plasma 9B obtained by centrifugal separation can be delivered from the introducing chamber 6 to the downstream chamber 7. FIG. 7 shows an example of the sequence in which the rotary drive unit 4 rotary drives the rotatable platform 2 to execute liquid delivery from the introducing chamber 6 into the downstream chamber 7.

Figure 8A:
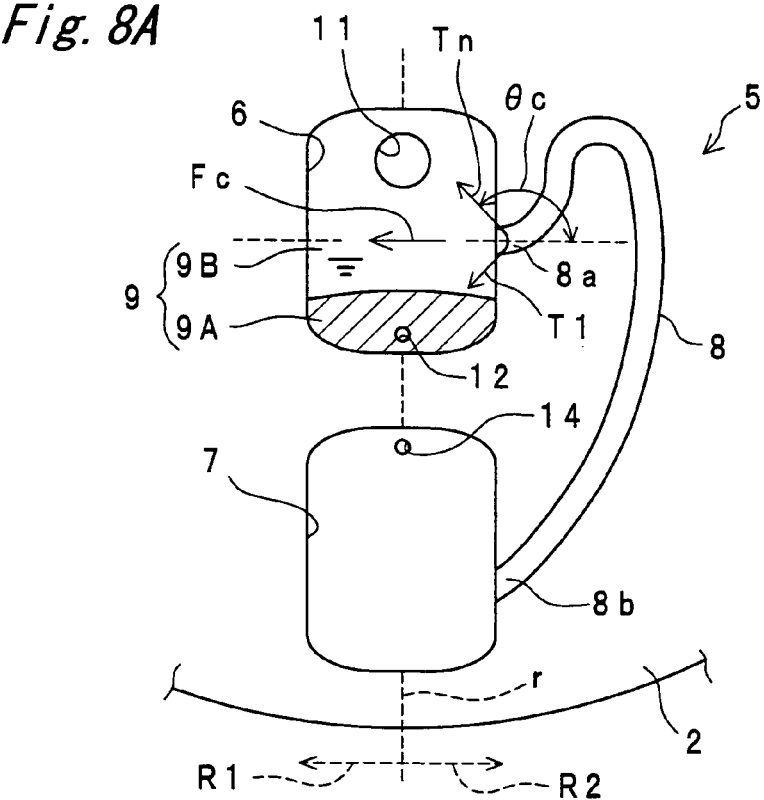
FIG. 8A is a schematic plan view for explaining the force acting on the blood plasma in the fluid passage end portion before the rotation of the rotatable platform is started.

Referring to FIG. 8A, as described above, the inlet end section 8a of the fluid passage 8 that is connected to the introducing chamber 6 has hydrophobic property and the fluid passage 8 is a micro fluid passage. Therefore, the blood plasma 9B is held in the inlet end section 8a by a capillary force Fc caused by surface tension, and the inside of the fluid passage 8 is not wetted with the blood plasma 9B. Because the fluid passage wall surface of the inlet end section 8a has hydrophobic properties, it is not wetted with the blood plasma 9B and the contact angle θc of the blood plasma 9B and the fluid passage wall surface is a dull angle. Therefore, a capillary force Fc in the direction of holding the blood plasma 9B inside the introducing chamber 6 is generated. More specifically, surface tension forces T1 to Tn are generated on the interface of the fluid passage wall surface and blood plasma 9B, and the capillary force Fc, which is the resultant force thereof, is generated in the clockwise direction R1, that is, in the direction form the inlet end section 8a toward the inside of the introducing chamber 6. The value of the capillary force Fc can be represented by the following formula (1).

$$Fc = T \times \cos \theta c \times c \quad (1)$$

Here, the reference symbol T stands for a surface tension of water, θc-a contact angle of the liquid with the fluid passage wall surface, and c-a circumferential length of the fluid passage.

Figure 8B:
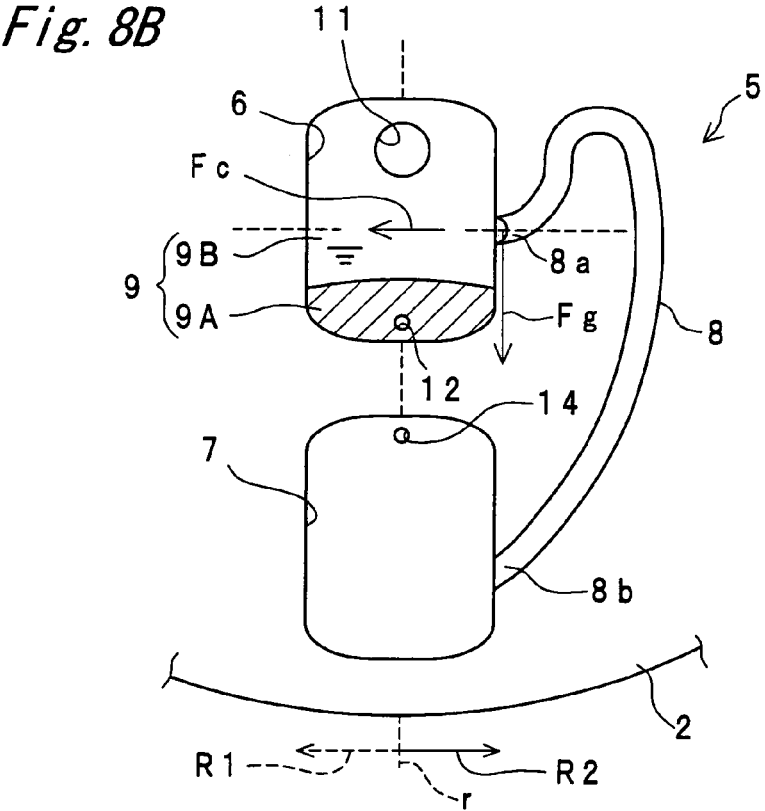
FIG. 8B is a schematic plan view for explaining the force acting on the blood plasma in the fluid passage end portion when the rotation of the rotatable platform is started.

From the time instant 0 to the time instant t1 shown in FIG. 7, the rotatable platform 2 is rotary driven with a velocity characteristic 41 having a gradual and constant acceleration a1 in the counterclockwise direction R2 (direction in which the inlet end section 8a extends from the introducing chamber 6). The rotation velocity of the rotatable platform 2 rises with the acceleration a1 and reaches the rotation velocity RV1 at the time instance t1. Referring also to FIG. 8B, a centrifugal force Fg acts outwardly in the radial direction r on the blood plasma 9B held by the capillary force Fc in the inlet end section 8a. However, the inlet end section 8a extends in the counterclockwise direction R2, and the action direction of the centrifugal force Fg is perpendicular to the extension direction of the inlet end section 8a. Therefore, despite the action of the centrifugal force Fg, the blood plasma 9B present in the inlet end section 8a is maintained in a state in which it is held by the capillary force Fc.

Figure 8C:
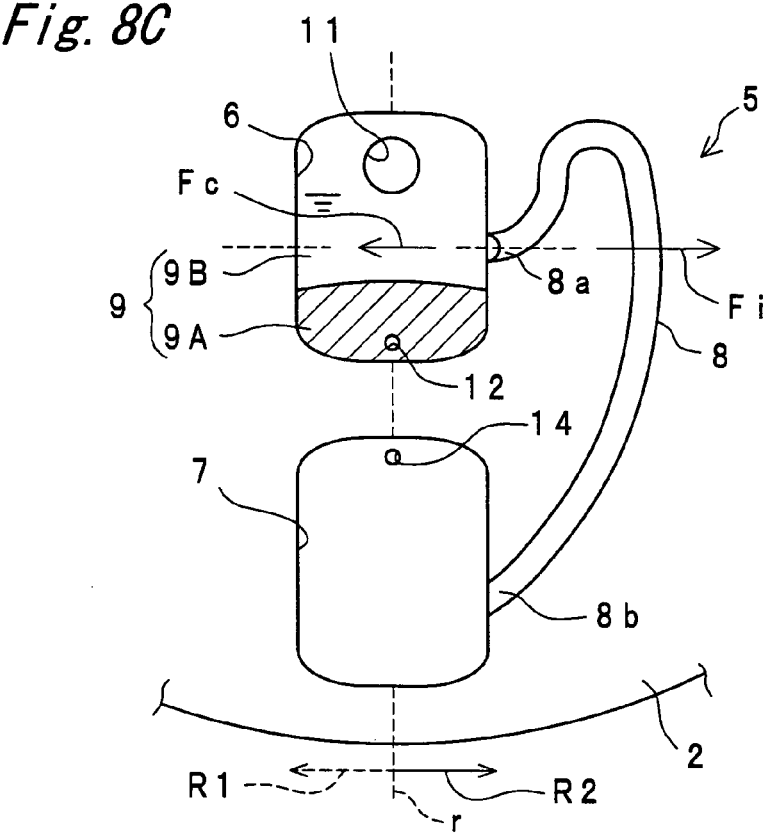
FIG. 8C is a schematic plan view for explaining the force acting on the blood plasma in the fluid passage end portion when the rotation of the rotatable platform is rapidly stopped.

Then, from the time instant t1 to the time instant t2 shown in FIG. 7, the rotatable platform 2 is abruptly braked according to the velocity characteristic 42 having a constant acceleration a2. Referring also to FIG. 8C, an inertial force Fi acts upon the blood sample 9 located in the inlet end section 8a due to abrupt braking of the rotatable platform 2. More specifically, if the rotatable platform 2 that is rotated in the counterclockwise direction R2 is abruptly braked, then the blood plasma 9B that has been accumulated in the introducing chamber 6 and was held in the inlet end section 8a will continue moving in the counterclockwise direction R2 due to the law of inertia. As a result, the inertial force Fi in the counterclockwise direction R2 will act upon the blood plasma 9B held in the inlet end section 8a. The value of the inertial force Fi is proportional to the absolute value of acceleration a2 occurring when the rotatable platform 2 is abruptly braked. The relationship represented by the following formula (2) is valid between the inertial force Fi and acceleration a2.

$$Fi = -m \times a2 \quad (2)$$

Here m stands for a mass of the liquid held in the inlet end section 8a. Furthermore, the minus sign in the right side of the formula indicates that the direction of the inertial force Fi is opposite to the direction of acceleration a2.

As described hereinabove, the inlet end section 8a extends in the counterclockwise direction R2 from the introducing chamber 6, and the capillary force Fc acts in the clockwise direction R1. Therefore, the inertial force Fi acts against the capillary force Fc in the direction of wetting the fluid passage 8 with the blood plasma 9B present in the inlet end section 8a. If the inertial force Fi becomes larger than the capillary force Fc, then the blood plasma 9B that has been held in the inlet end section 8a will flow into the fluid passage 8.

Figure 8D:
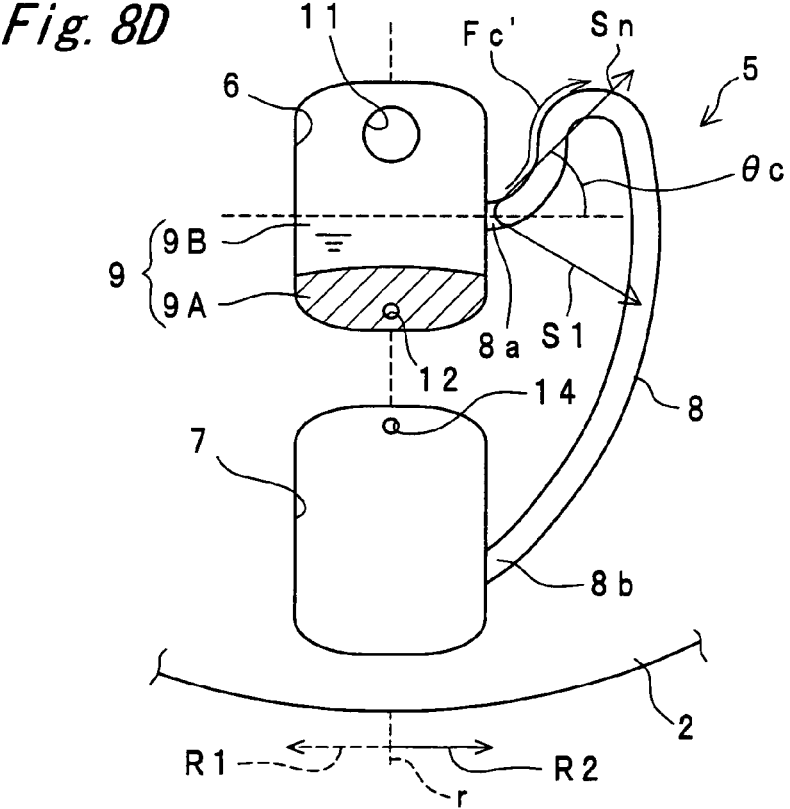
FIG. 8D is a schematic plan view for explaining the force acting on the blood plasma in the fluid passage end portion during delivery.

As shown in FIG. 8D, if the fluid passage wall surface of the fluid passage 8 having hydrophilic properties is wetted, the contact angle θc of the blood plasma 9B and fluid passage wall surface becomes an acute angle. Surface tension forces S1 to Sn are generated in the direction shown in the figure at the interface of the fluid passage wall surface and blood sample 9, and the capillary force Fc', which is the resultant force thereof, is generated in the counterclockwise direction R2, that is in the direction in which the inlet end section 8a extends from the introducing chamber 6. Therefore, holding with the inlet end section 8a is cancelled and the capillary force Fc' acting upon the blood sample 9 that flowed into the fluid passage 8 acts in the direction of filling the fluid passage 8 with the blood sample 9. The value of the capillary force Fc' is represented in the same manner as by the above-described formula (1).

If the blood sample 9 is introduced into the downstream chamber 7 via the fluid passage 8, the air present in the downstream chamber 7 is drained to the outside of the rotatable platform 2 via the air port 14 as the volume of the blood sample 9 in the downstream chamber 7 increases.

Figure 9:
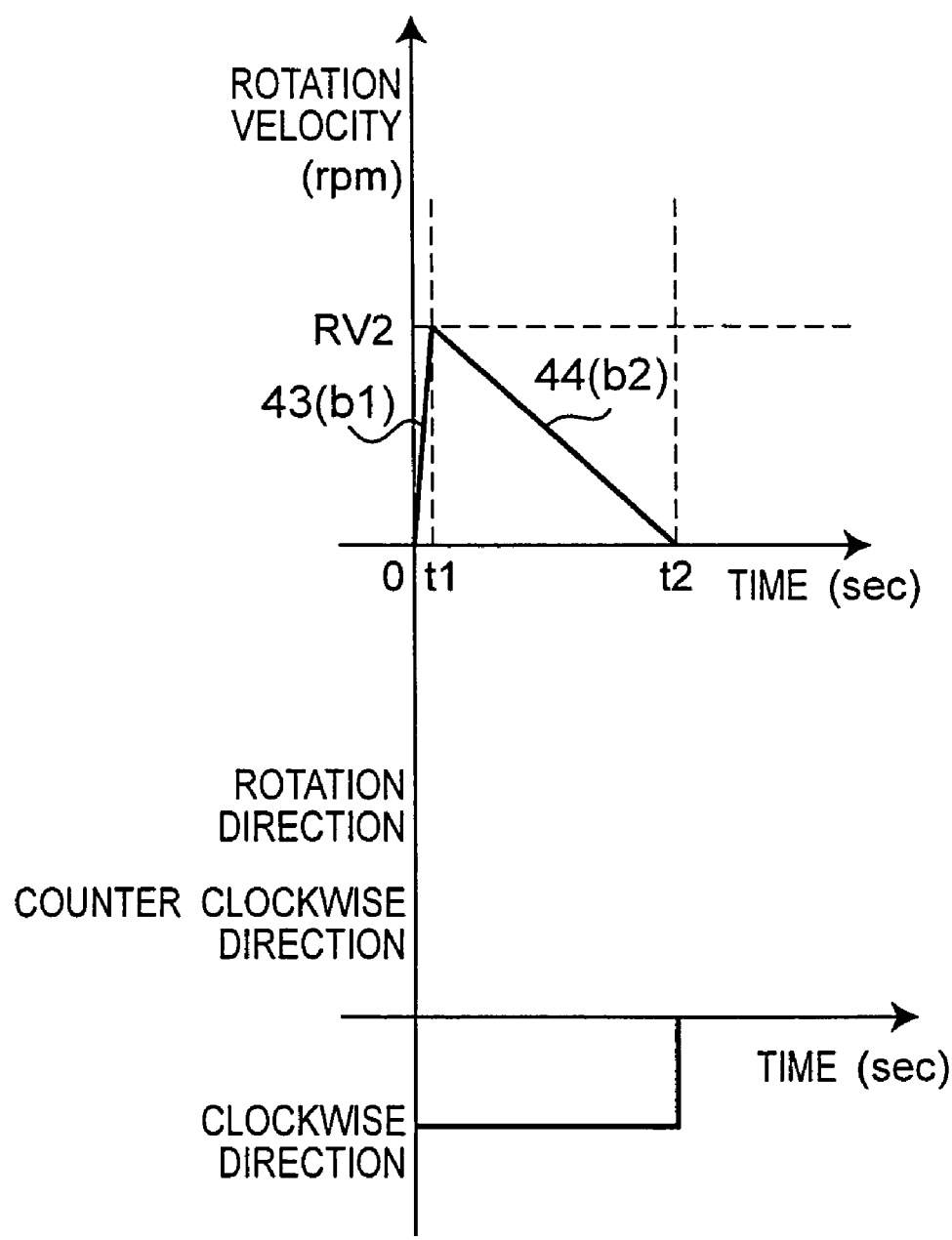
FIG. 9 is a diagram illustrating the velocity waveform and rotation direction of a second example of delivery operation of the blood analysis apparatus of the first embodiment of the present invention.
Figure 10A:
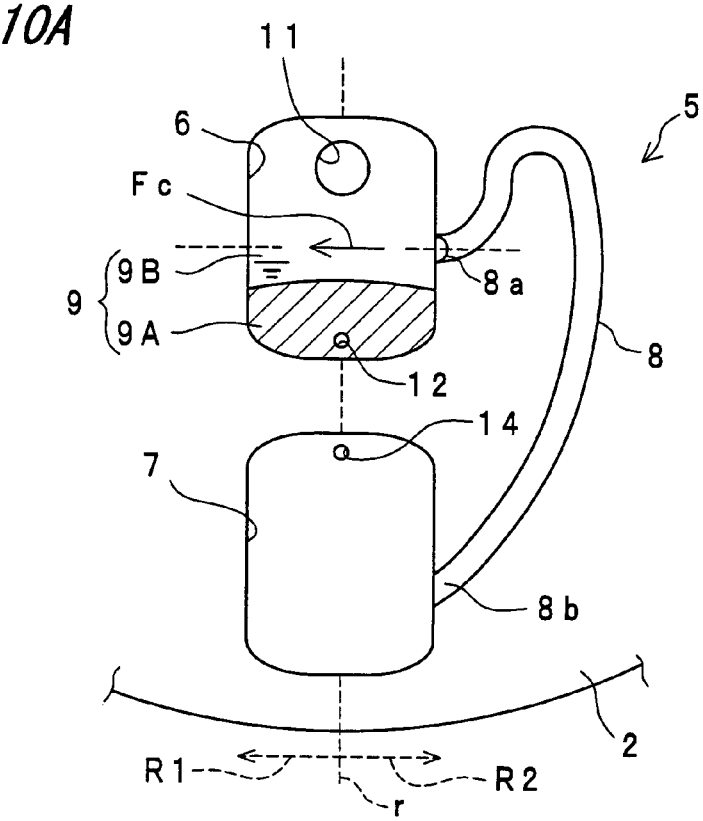
FIG. 10A is a schematic plan view for explaining the force acting on the blood plasma in the fluid passage end portion before the rotation of the rotatable platform is started.

FIG. 9 shows another example of the sequence by which the rotary drive unit 4 rotary drives the rotatable platform 2 in order to execute the delivery from the introducing chamber 6 to the downstream chamber 7. Referring also to FIG. 10A, because the inlet end section 8a has hydrophobic properties, the capillary force Fc in the clockwise direction R1 that is opposite to the extension direction of the inlet end section 8a (counterclockwise direction R2) acts upon the blood plasma 9B located in the inlet end section 8a. The blood plasma 9B located in the introducing chamber 6 is held in the inlet end section 8a by this capillary force Fc.

Figure 10B:
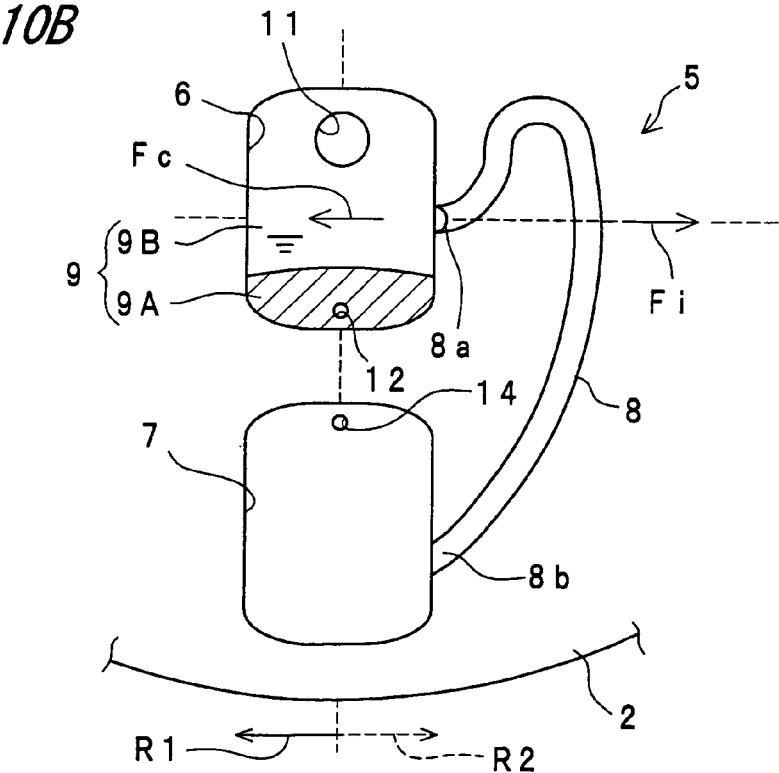
FIG. 10B is a schematic plan view for explaining the force acting on the blood plasma in the fluid passage end portion during rapid rotation of the rotatable platform.
Figure 10C:
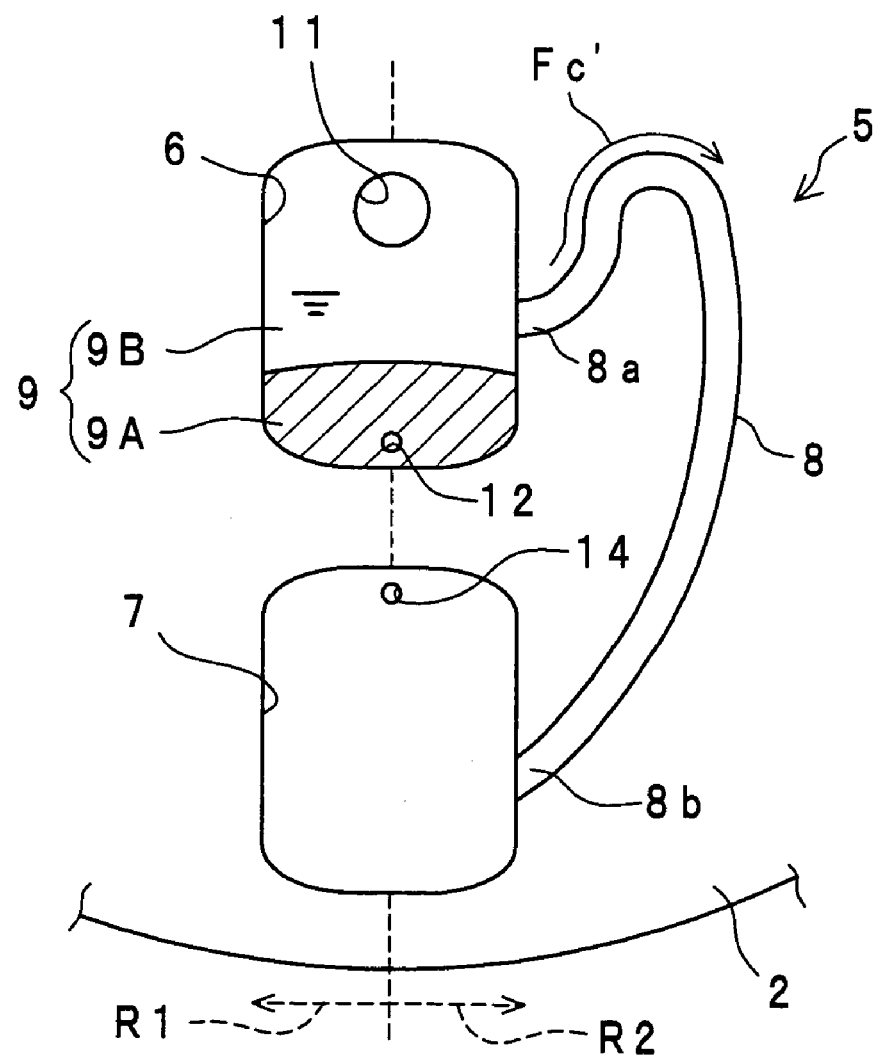
FIG. 10C is a schematic plan view for explaining the force acting on the blood plasma in the fluid passage end portion during delivery.

From the time instant 0 to the time instant t1 shown in FIG. 9, the rotatable platform 2 in a stationary state thereof is rapidly rotary driven with a velocity characteristic 43 having a constant acceleration b1 in the clockwise direction R1 (direction opposite to the direction in which the inlet end section 8a extends from the introducing chamber 6. At the time instant t1, a rotation velocity RV2 is attained. As shown in FIG. 10B, an inertial force Fi acts upon the blood plasma 9B located in the inlet end section 8a due to rapid rotation in the clockwise direction R1. More specifically, even though the rotatable platform 2 starts rotating in the clockwise direction R1, the blood plasma 9B that has been accumulated in the introducing chamber 6 and held in the inlet end section 8a maintains a stationary state thereof due to the law of inertia. As a result, an inertial force Fi in the counterclockwise direction R2 acts upon the blood plasma 9B held in the inlet end section 8a. The value of the inertial force Fi is proportional to the absolute value of the acceleration b1 during rapid rotation or the rotatable platform 2. This inertial force Fi acts against the capillary force Fc in the direction of wetting the fluid passage 8 with the blood plasma 9B located in the inlet end section 8a. If the inertial force Fi exceeds the capillary force Fc, the blood plasma 9B held in the inlet end section 8a flows into the fluid passage 8. Because the fluid passage 8 and the introducing chamber 6 have hydrophilic properties, once holding in the inlet end section 8a is canceled, a capillary force Fc' directed toward the downstream chamber 7 acts upon the blood sample 9, as shown in FIG. 10C, and the blood plasma 9B flows into the downstream chamber 7 via the fluid passage 8.

Then, from the time instant t1 to the time instant (solid line) in FIG. 9, the rotatable platform 2 is braked according to the velocity characteristic 44 having a gradual and constant acceleration b2.

As described above, the blood plasma 9B located in the introducing chamber 6 can be delivered into the downstream chamber 7 via the fluid passage 8 by abruptly braking or rapidly rotating the rotatable platform 2 with the rotary drive unit 4 so that the inertial force Fi exceeding the capillary force Fc holding the blood sample 9 inside the introducing chamber 6 acts on the blood plasma 9B located in the inlet end section 8a of the fluid passage 8.

The blood processing apparatus 1 of the present embodiment is useful as an analyzer for analyzing bioingredients, e.g., proteins contained in blood. In particular, blood samples are separated into blood cells and blood plasma at a preliminary stage, and proteins contained in blood plasma are the analytes assayed. Furthermore, because the blood cells—blood plasma separation is centrifugal separation using a centrifugal force, the separation can be easily combined with liquid delivery via the fluid passage 8 caused by rapid rotation or abrupt braking of the rotatable platform 2. Moreover, supporting a reagent, etc., in each chamber or implementing physical operations such as heating on each chamber makes it possible to provide functions such as reactions, purification, and detection. Therefore, the blood processing apparatus 1 of the present embodiment can be also applied, e.g., to POCT diagnostic biosensors for conducting separation, purification, reactions, and detection of proteins or health indicators contained in blood samples. Because the air port 11 of the introducing chamber 6 is sealed by solidifying the blood sample introduced into the chamber by bringing the sample into contact with a blood coagulator, operations can be carried out without special steps such as pasting a sheet piece for sealing the air port 11. As a result, the time required for treating, e.g., analyzing, the blood can be shortened. Furthermore, operations are conducted in an automated mode in a simple manner, and safety of the operator can be ensured when blood, which can be contagious, is handled.

A variety of alternatives relating to the structure of the blood processing apparatus 1 will be described below. Those alternatives are not limited to the first embodiments and can be also applied to the below-described second to fourth embodiments.

The external shape of the rotatable platform 2 is not limited to a disk and the rotatable platform may be in the form of a cube or rectangular parallelepiped or have a polygonal, e.g. pentagonal, or star-like shape.

The shape of the air port 12 of the introducing chamber 6 is not limited to a round shape and may have another shape, e.g., an elliptical or polygonal shape. As for the size of the air port 12, the diameter or representative length thereof is preferably set within a range of 10 µm or more to 3 mm or less. The air port 12 is preferably provided in one place and has a cylindrical shape with a diameter of 100 µm or more to 1000 µm or more. In this case coagulation of blood platelets present in the blood is realized 10 to 12 sec after the blood sample 9 is injected from the injection port 11, scattering of blood caused by rotation is prevented and the air port 12 can be reliably sealed to withstand the action of a centrifugal force.

The number and arrangement of introducing chambers 6, downstream chambers 7, and fluid passages 8 in each fluid passage site 5 are not limited to those shown in FIG. 2.

Alternatives of the laminated structure of the rotatable platform 2 will be described below.

A rotatable platform 2 of the first alternative shown in FIG. 11 has a three-layer structure comprising an upper platform 21, a fluid passage platform 23, and a bottom platform 24. An injection port 11 and air ports 12, 14 are provided in the upper platform 21. Groove holes 23a of the shape corresponding to the introducing chamber 6, downstream chamber 7, and a fluid passage 8 are provided in the fluid passage platform 22. Concave portions 24a, 24b having a bottom and constituting the bottom sections of the introducing chamber 6 and downstream chamber 7 are formed in the bottom platform 24. With such a configuration, the depth of the fluid passage 8, introducing chamber 6, and downstream chamber 7 can be easily changed. Furthermore, because the bottom sections of the introducing chamber 6 and downstream chamber 7 are formed independently from each other in the bottom platform 24, a reagent can be readily supported on the bottom sections of the introducing chamber 6 and downstream chamber 7 by supporting the reagent capable of reacting with the blood sample 9 in the prescribed position of the bottom platform before the platforms are joined.

Figure 12:
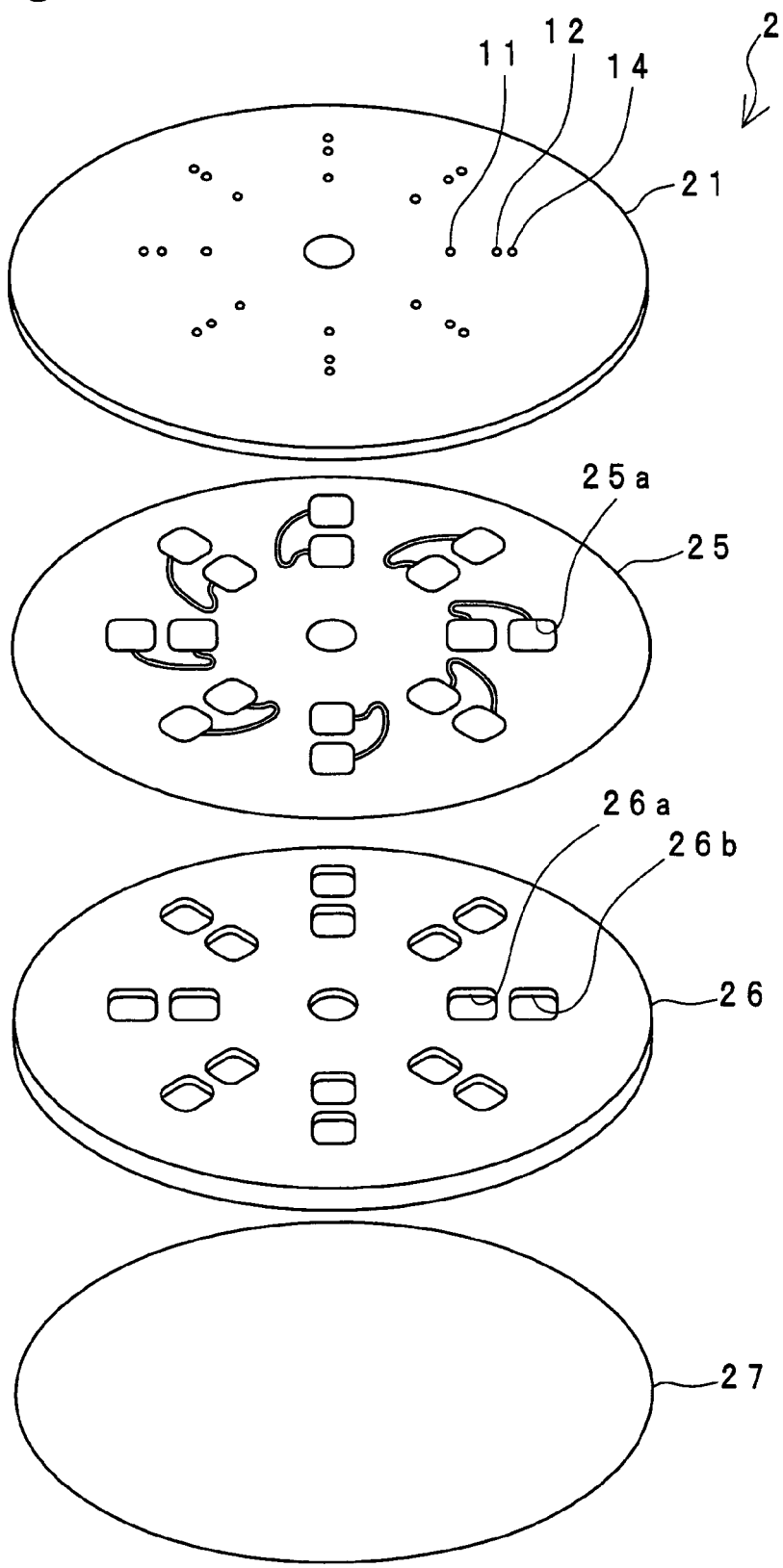
FIG. 12 is an exploded perspective view illustrating a second alternative of the rotatable platform.

The rotatable platform 2 of the second alternative shown in FIG. 12 has a four-layer structure in which an upper platform 21, a fluid passage platform 25, a chamber platform 26, and a bottom platform 27 are bonded in a laminated state thereof. The injection port 11 and air ports 12, 14 are provided in the upper platform 21 so as to pass therethrough in the plate thickness direction. Groove holes 25a of the shape corresponding to the introducing chamber 6, downstream chamber 7, and fluid passage 8 and passing through in the plate thickness direction are provided in the fluid passage platform 25. Groove holes 26a, 26b of the shape corresponding to the introducing chamber 6 and downstream chamber 7 and passing through in the plate thickness direction are provided in the chamber platform 26. The bottom platform 27 constitutes the bottom surface of the introducing chamber 6 and downstream chamber 7 and is not provided with grooves or holes. The rotatable platform 2 of such multilayer structure can be manufactured by joining the platforms and, therefore, excellent productivity can be attained. Furthermore, the depth of the fluid passage 8 is determined by the thickness of the fluid passage platform 22, and the depth of the introducing chamber 6 and downstream chamber 7 is determined by the combined thickness of the fluid passage platform 22 and chamber platform 26. Therefore, a structure can be easily fabricated in which the depth of the fluid passage 8 is less than the depth of the introducing chamber 6 and downstream chamber 7, and the depth of the fluid passage 8 and the depth of the introducing chamber 6 and downstream chamber 7 can be set independently from each other. For example, when the depth of the fluid passage 8 is approximately 100 μm, a sheet-like fluid passage platform 25 in which the shape of the fluid passage 8, introducing chamber 6, and downstream chamber 7 is cut through can be used. Therefore, this is preferred from the standpoint of productivity. Furthermore, because the bottom platform 27 constituting the bottom wall of the introducing chamber 6 and downstream chamber 7 is a body separate from other platforms, a reagent can be easily supported on the lower surface platform 24 prior to joining.

Alternatives of the wetting property of the introducing chamber 6, downstream chamber 7, and fluid passage 8 will be explained below.

As the first alternative, in order to improve productivity, the entire fluid passage 8, rather than the inlet end section 8a, may be hydrophobic.

As the second alternative, the entire fluid passage site 5 may have hydrophobic properties. Because the entire fluid passage site 5 may be composed of a hydrophobic material or the entire fluid passage site 5 may be subjected to a treatment providing it with hydrophobic properties, productivity can be increased.

As the third alternative, the entire rotatable platform 2 may have hydrophobic properties. Because the entire rotatable platform 2 may be composed of a hydrophobic material or the entire rotatable platform 2 may be subjected to a treatment providing it with hydrophobic properties, productivity can be increased.

Second Embodiment

Figure 13:
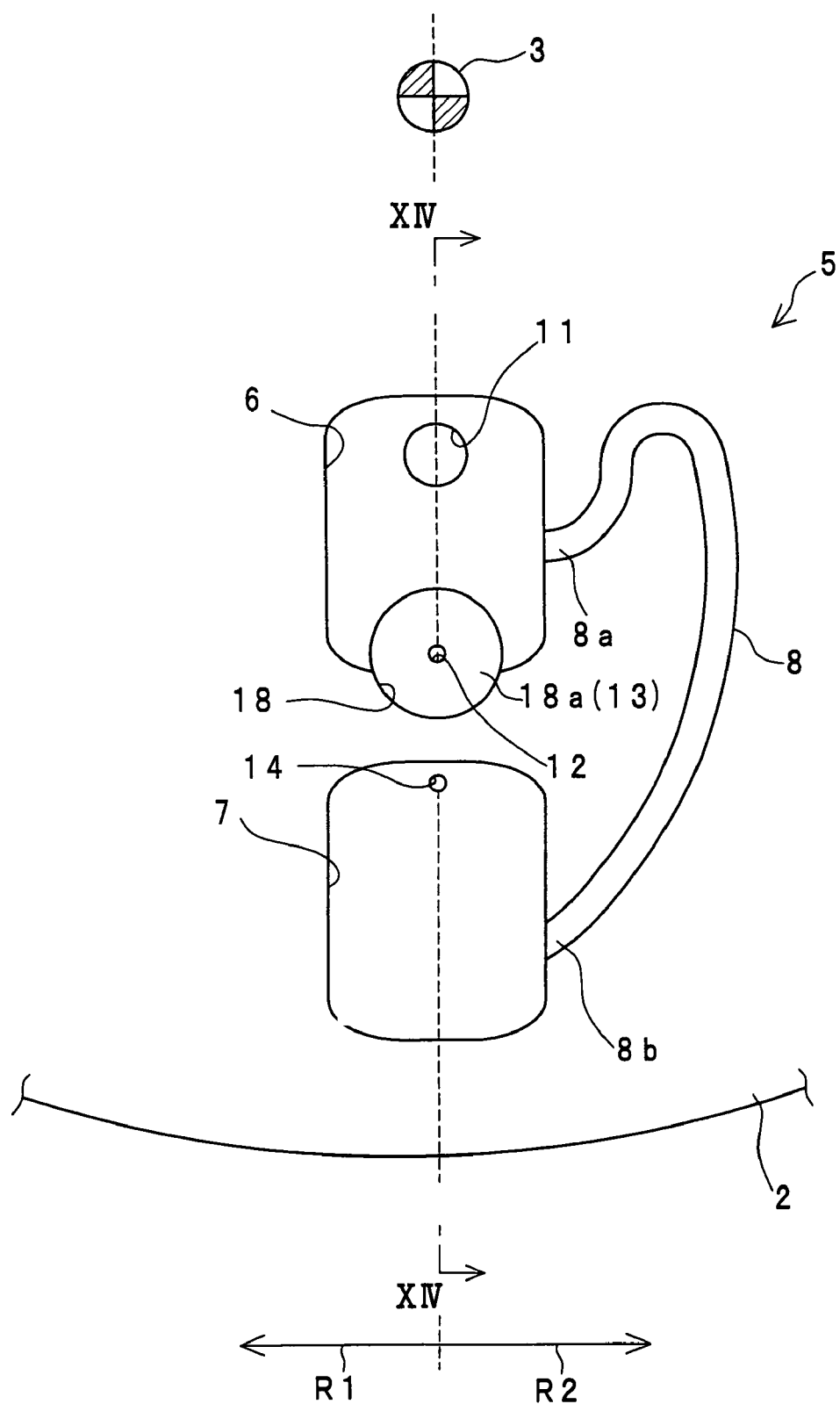
FIG. 13 is a partially enlarged plan view of the rotatable platform of the blood analysis apparatus of a second embodiment of the present invention.
Figure 14:
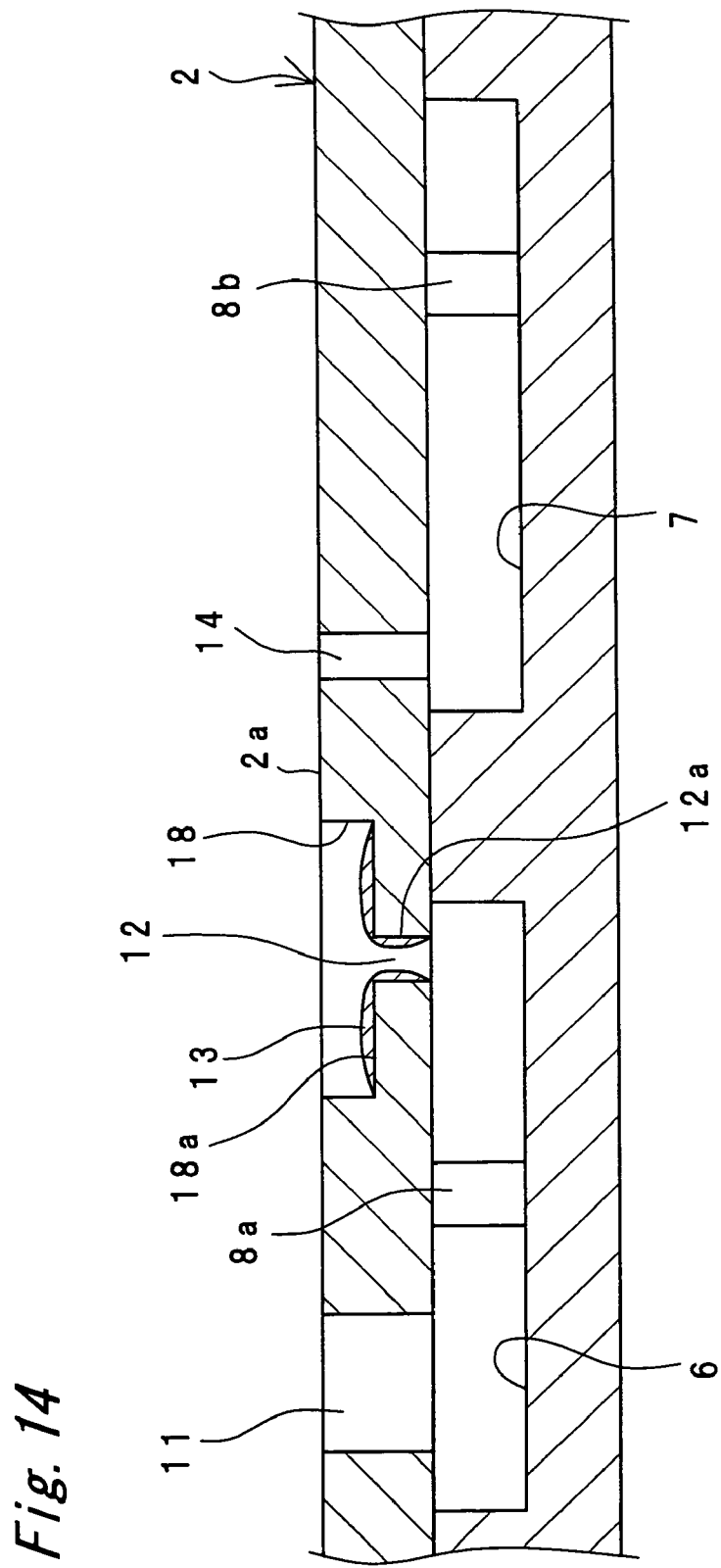
FIG. 14 is a partial cross section along the XIV-XIV line in FIG. 13.

In the blood processing apparatus 1 of the second embodiment of the present invention shown in FIG. 13 and FIG. 14, a step is provided in the air port 12 on the side of the surface 2a of the rotatable platform 2. More specifically, the air port 12 is open at the bottom wall 18a in the surface 2a of the rotatable platform 2, and a holding concave portion 18 is formed such that the surface area of the bottom wall 18a is larger than the surface area of the air port 12. In the present embodiment, the holding concave portion 18 has a round shape in the plan view thereof. The blood coagulant 13 is held around the port wall surface 12a of the air port 12 and around the air port 12, that is on the bottom wall 18a of the holding concave portion 18.

Holding the blood coagulant 13 on the bottom wall 18a of the holding concave portion 18 increases the surface area of the blood coagulant 13 and also increases the contact surface area of the blood coagulant 13 and blood sample 9. As a result, coagulation of blood platelets in the blood occurs more rapidly, and the air port 12 can be more strongly sealed with the coagulated blood. Therefore, the time from the introduction of the blood sample 9 into the introducing chamber 6 to the sealing of the air port 12 can be shortened and a more rapid transition can be made to the next blood processing operation such as separation of blood cells and blood plasma. Furthermore, scattering of the blood sample 9 located in the introducing chamber 6 from the air port 12 by the centrifugal force when blood processing such as centrifugal separation is conduced can be prevented more reliably.

No specific limitation is placed on the shape of the holding concave portion, as long as the surface area of the bottom wall 18a is more than the surface area of the air port 12. However, the round shape in the plan view, such as shown in FIG. 13 is preferred. Furthermore, it is preferred that the surface area of the bottom wall 18a of the holding concave portion 18 be 0.015 mm$^2$ or more to 30 mm$^2$ or less. With such a surface area, the air port 12 can be rapidly sealed after the blood sample 9 has been introduced into the introducing chamber 6. Therefore, the rotatable platform 2 can be immediately rotated, without waiting. In this case, within the initial 3 sec, the rotation velocity is preferably set to 1000 rpm or less. When the bottom wall 18a has a round shape, as in the present embodiment, the diameter corresponding to the preferred surface area is from 50 μm to approximately 3 mm.

Other features and operation of the second embodiment are identical to those of the first embodiment.

Third Embodiment

Figure 15:
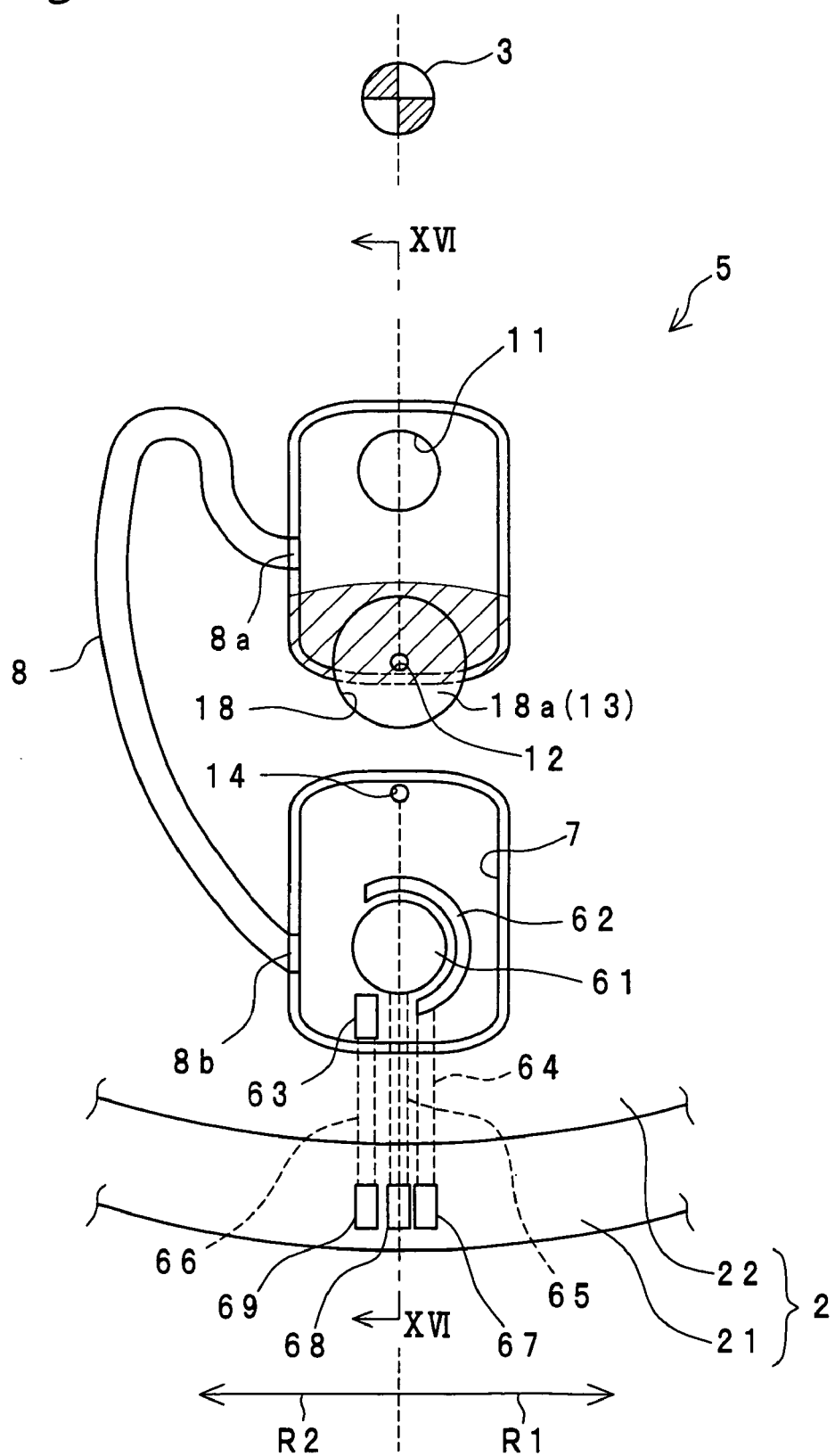
FIG. 15 is a partially enlarged plan view of the rotatable platform of the blood analysis apparatus of a third embodiment of the present invention.
Figure 16:
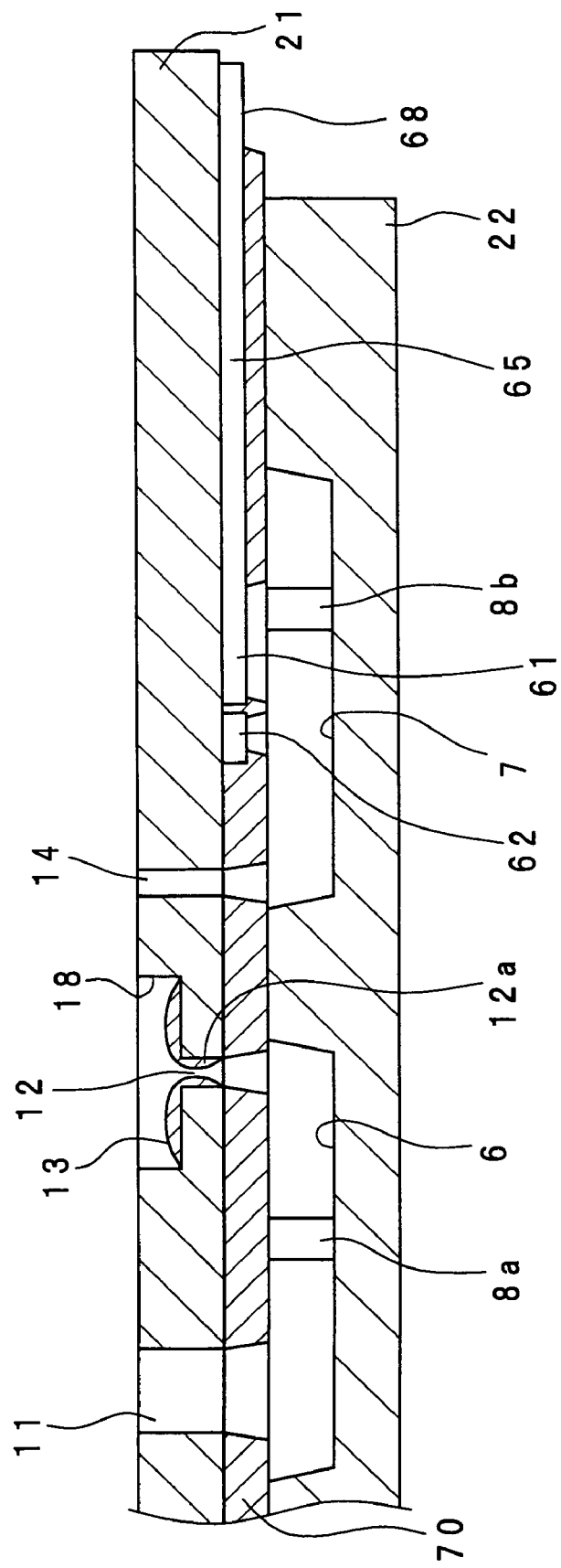
FIG. 16 is a partial cross section along the XVI-XVI line in FIG. 15.

A blood processing apparatus 1 of the third embodiment of the present invention that is shown in FIG. 15 and FIG. 16 is a blood component analysis apparatus for conducting electrochemical analysis of a blood sample 9.

Detection electrodes of three types, that is, a working electrode 61, a counter electrode 62, and a reference electrode 63, are disposed inside a downstream chamber 7 functioning as a detection chamber. More specifically, those working electrode 61, counter electrode 62, and reference electrode 63 are provided in sites constituting the upper wall of the downstream chamber 7 of the upper platform 21. The working electrode 61, counter electrode 62, and reference electrode 63 are electrically connected to electrode terminals 67, 68, 69 by respective lead wires 64, 65, 66. A reaction reagent is supported inside the downstream chamber 7. An insulating film 70 is introduced between the upper platform 21 and a lower platform 22.

In the present embodiment, the working electrode 61, counter electrode 62, and reference electrode 63 are formed by a thin film formation technique such as vapor deposition or sputtering. The working electrode 61 has a round shape, the counter electrode 62 has a circular arc shape, and the counter electrode 62 has a rectangular shape. However, the working electrode 61, counter electrode 62, and reference electrode 63 may have any shape. For example, those electrodes may be obtained by inserting electrode wires into the downstream chamber 7.

The working electrode 61, counter electrode 62, and reference electrode 63 are preferably from materials with stable electrochemical properties; gold, platinum, carbon, tungsten, silver, and copper are mainly suitable therefore. The reference electrode 63 serving as a voltage standard is preferably configured as a silver or silver—silver chloride electrode. The reference electrode 63 can be obtained as a silver or silver—silver chloride electrode by coating a silver paste on the electrode material constituting the working electrode 61 and counter electrode 62, then covering again with silver, and electroplating.

The insulating film 70 covers the lead wires 67 to 69 and has a function of regulating the surface area of the working electrode 61, counter electrode 62, and reference electrode 63. In particular, the surface area of the working electrode 61 has to be determined with especially high accuracy. The insulating film 70 also has a function of eliminating the step between the sites on the lower surface of the lower platform 21 where the working electrode 61, counter electrode 62, and reference electrode 63 are formed and the sites where those electrodes are not formed, thereby flattening the lower surface of the lower platform 21.

If the blood sample 9 is introduced from an injection port 11 into an introducing chamber 6, the air located in the introducing chamber 6 is drained from an air port 12, and the blood sample 9 can be introduced into the entire introducing chamber 6. Furthermore, the blood sample 9 is coagulated with a blood coagulant 13 and the air port 12 is closed. The blood sample 9 is then separated into blood cells 9A and blood plasma 9B by centrifugal separation. Because the air port 12 is sealed with the coagulated blood sample 9 during centrifugal separation, the blood plasma 9B is not scattered. If the rotary drive unit 4 then abruptly brakes or rapidly rotates the rotatable platform 2, thereby generating an inertial force Fi exceeding a capillary force Fc by which the end section 8a of the fluid passage 8 holds the blood plasma 9B inside the introducing chamber 6, then the blood plasma 9B located inside the introducing chamber 6 is delivered into the downstream chamber 7 via the fluid passage 8. The blood plasma 9B that was delivered into the downstream chamber 7 reacts with a reagent held inside the downstream chamber 7, and an electrochemical (redox) reaction proceeding at this time is measured with the working electrode 61, counter electrode 62, and reference electrode 63.

The blood processing apparatus 1 of the present embodiment was actually fabricated and the analysis of blood sample was conducted. An electron donor-acceptor 4-aminophenyl phosphate (referred to hereinbelow as pAPP), ALP (alkali phosphatase) labeled anti-CRP antibody, and a Tris buffer (pH 8.0) were dried and supported in advance in the downstream chamber 7. The blood sample 9 introduced from the injection port 11 into the introducing chamber 6 was coagulated with the blood coagulant 13 and spontaneously closed the air port 12. When the rotatable platform was rotated for 10 min at a rotation velocity of 2500 rpm, the blood cells 9A and blood plasma 9B were clearly separated. Furthermore, by abruptly braking the rotatable platform 2, the blood plasma 9B in an amount of approximately 30 μL was delivered from the introducing chamber 6 into the downstream chamber 7 via the fluid passage 8. The blood plasma 9B that has flowed into the downstream chamber 7 started a reaction represented by the following reaction formula with the aforementioned reagent within 5 min, the pAPP was subjected to dephosphorylation with ALP and produced 4-aminophenol (referred to hereinbelow as pAP).

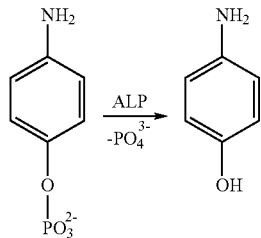

An electric potential of +400 mV was then provided to the working electrode 61. This electric potential converted the pAP from a reduced material into an oxidized material. Electrons were transferred to the electrode in this process. When an electric current flowing in the working electrode 61 at this time was measured, a current response of 1 nM to 1 μM, which depended on the quantity of CRP antigen contained in the blood plasma, was obtained. The blood processing apparatus 1 of the third embodiment was thus confirmed to be capable of obtaining information suitable for predicting the disease and evaluating the health state.

In the present embodiment, the detection electrode has a three-electrode structure comprising the working electrode 61, counter electrode 62, and reference electrode 63 and can measure not only the voltage or voltage variation, but also the absolute value of the voltage. However, the detection electrode may also have a two-electrode structure comprising a working electrode and a counter electrode. The two-electrode structure cannot measure the voltage or absolute value of the voltage, but is easy to manufacture.

Other structural features and operation of the third embodiment are identical to those of the second embodiment.

Fourth Embodiment

Figure 17:
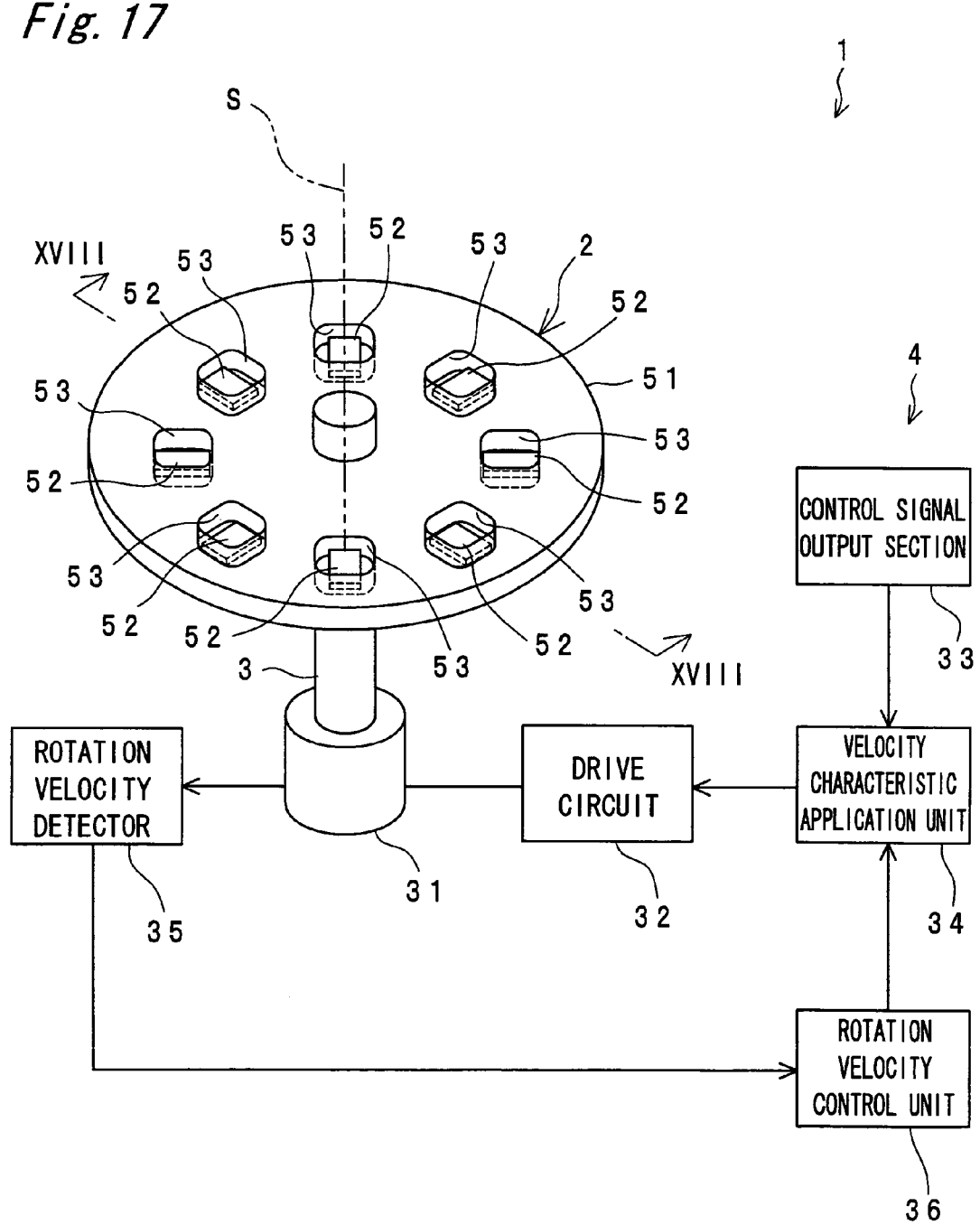
FIG. 17 is a schematic structural view illustrating the blood analysis apparatus of a fourth embodiment of the present invention.
Figure 18:
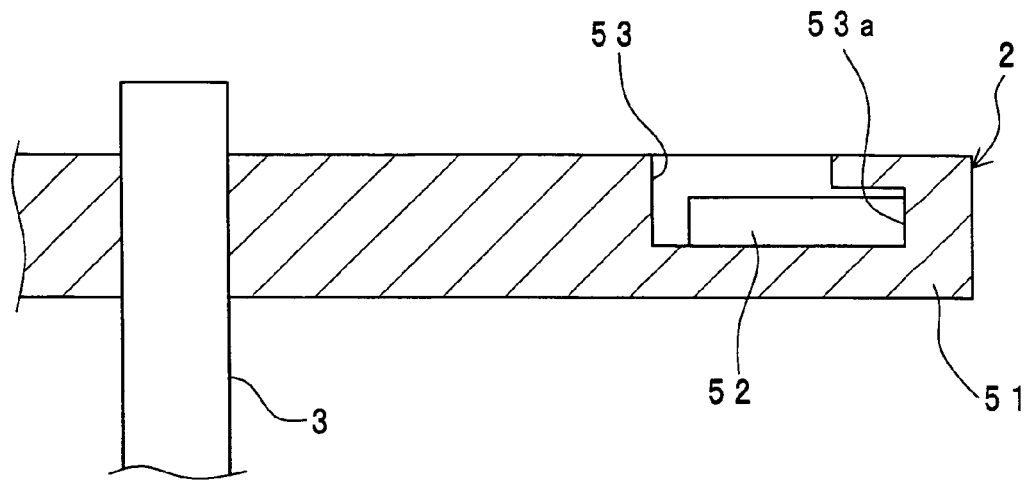
FIG. 18 is a partial cross section along the XVII-XVII line in FIG. 17.
Figure 19:
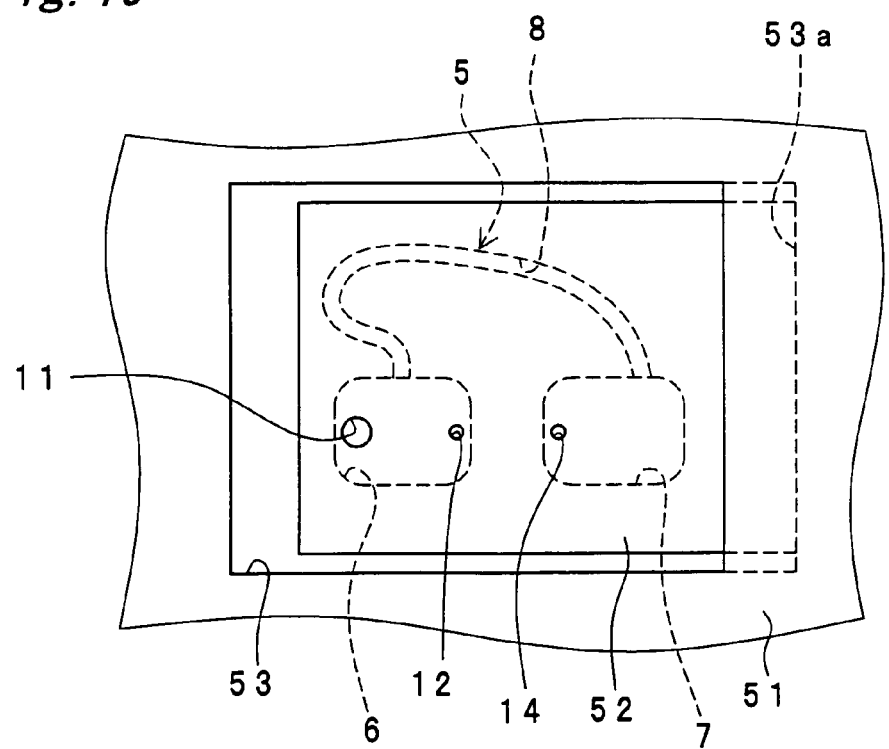
FIG. 19 is a partially enlarged plan view of the rotatable platform of the blood analysis apparatus of the fourth embodiment of the present invention.
Figure 20:
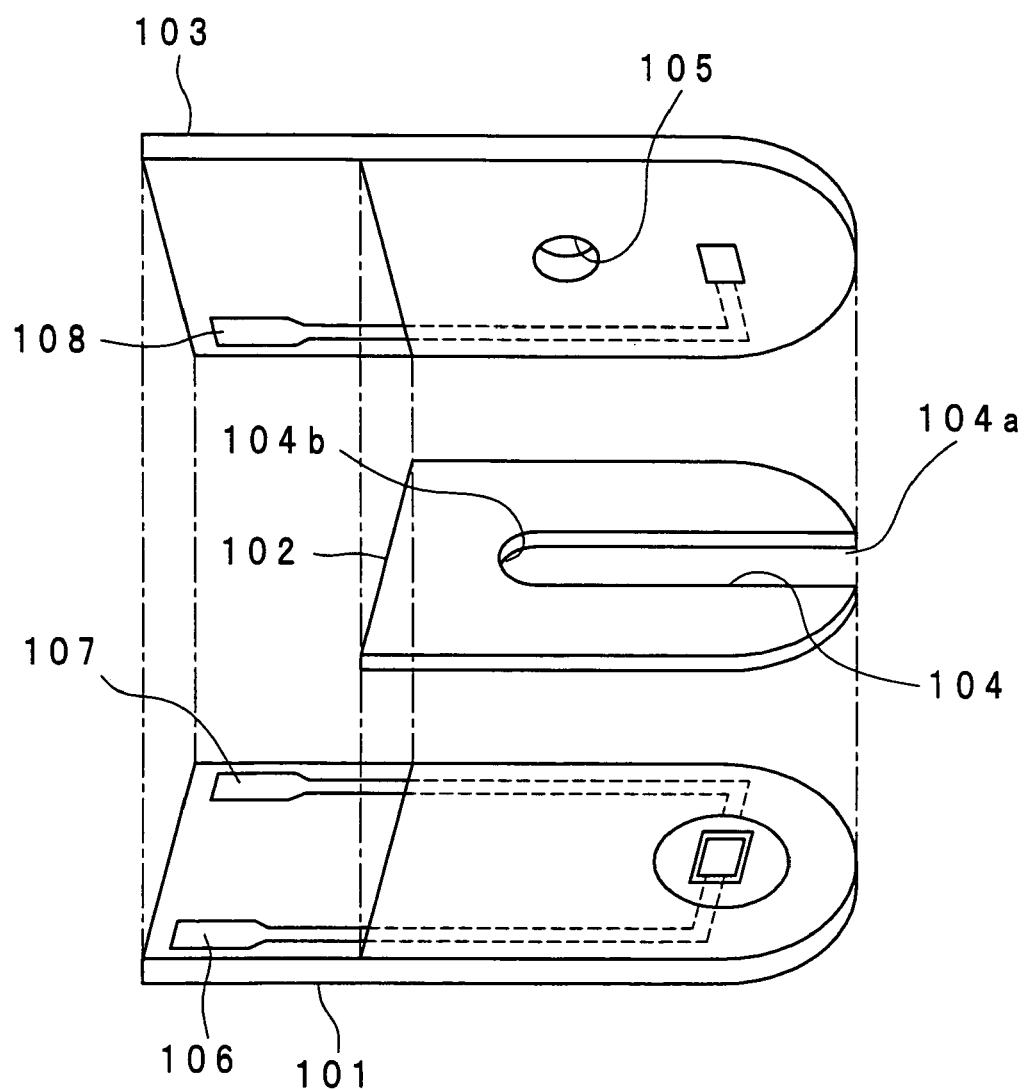
FIG. 20 is an exploded perspective view illustrating a biosensor that is an example of the conventional blood analysis apparatus.
Figure 21:
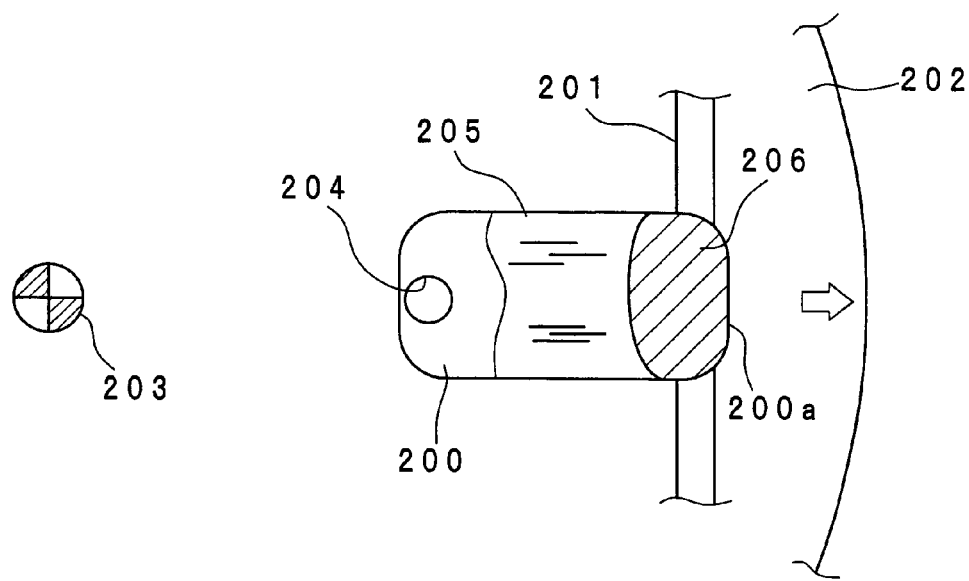
FIG. 21 is a schematic drawing for explaining the problems arising when a micro fluid passage is used as an air port.

In the blood processing apparatus 1 of the fourth embodiment of the present invention shown in FIG. 17 to FIG. 19, the structure of the rotatable platform 2 is different from that of the first embodiment. More specifically, the rotatable platform 2 comprises a rotatable platform body 51 and chip bodies 52 that can be attached to the rotatable platform body 51 and detached therefrom. Fluid passage sites 5 are not formed in the rotatable platform body 51, but fluid passage sites 5 are formed in each chip body 52. A plurality of accommodation holes 53 for accommodating the chip bodies 52 are formed in the upper surface side of the rotatable platform body 51. The accommodation openings 53 are disposed radially with respect to the rotation shaft 3. Concave portions 53a are formed in the wall surface on the outer side of the accommodation holes 53. The chip bodies 52 are held inside the accommodation holes 53 by arranging parts of chip bodies 52 inside the concave portions 53a. In particular, because the chip bodies 52 are impelled toward the concave portions 53a by a centrifugal force when the rotatable platform 2 is rotated, the chip bodies 52 are reliably held in the rotatable platform body 51, without falling out of the accommodation holes 53.

Other structural features and operation of the fourth embodiment are identical to those of the first embodiment.

What is claimed is:
1. A blood processing apparatus comprising:
a platform;
a first chamber formed inside the platform;
an injection port formed in the platform, communicating the first chamber with an outside of the platform, and adapted to introduce a blood sample into the first chamber;
an air port formed in the platform and communicating the first chamber with the outside of the platform; and
a blood coagulant held on a port wall surface of the air port and/or around a portion of a surface of the platform where the air port is opened.
2. The blood processing apparatus according to claim 1, wherein the blood coagulant comprises at least one substance for initiating coagulation of the blood sample or aggregation of blood platelets in the blood sample.
3. The blood processing apparatus according to claim 1, wherein the blood coagulant comprises calcium ions or ionomycine of not less than 0.2 μmol and not more than 2 mmol.

4. The blood processing apparatus according to claim 1, wherein the blood coagulant comprises at least one of tissue thromboplastin, partial thromboplastin, activated partial thromboplastin, and activated cephaloplastin.

5. The blood processing apparatus according to claim 1, wherein the blood coagulant comprises at least one of thrombin, epinephrine, a blood platelet activating factor, ristocetin, a thrombin receptor-sensitive peptide, and arachidonic acid.

6. The blood processing apparatus according to claim 1, wherein the blood coagulant has hydrophilic property.

7. The blood processing apparatus according to claim 1, further comprising a holding concave portion formed in the surface of the platform, a bottom wall of the holding concave portion being communicated with the air port and having an area larger than that of the air port,
wherein the blood coagulant is held at least around the air port on the bottom wall of the holding concave portion.

8. The blood processing apparatus according to claim 1, wherein the platform is capable of rotating around a central axis of rotation;
wherein the blood processing apparatus further comprises a rotary drive unit capable of rotatably driving the platform around the central axis of rotation,
wherein the injection port is formed in a site of the first chamber on a side of the central axis of rotation; and
wherein the air port is formed in a site of the first chamber farther from the central axis of rotation than the injection port.

9. The blood processing apparatus according to claim 8, further comprising:
a second chamber formed inside the platform, and
a fluid passage formed inside the platform and communicating the first chamber with the second chamber,
wherein a fluid passage end portion of the fluid passage connected to the first chamber is disposed closer to the central axis of rotation of the platform than the air port.

10. The blood processing apparatus according to claim 9, wherein the fluid passage end portion of the fluid passage connected to the first chamber extends in a rotation direction of the platform, and holds the liquid sample in the first chamber by a capillary force, and
wherein the rotary drive unit is capable of rotatably driving the platform around the central axis of rotation so that an inertial force exceeding the capillary force acts upon the blood sample in the fluid passage end portion.

11. The blood processing apparatus according to claim 9, further comprising a detection electrode for analyzing a blood component in the second chamber.

12. The blood processing apparatus according to claim 9, wherein the platform comprises a first platform having the injection port and the air port formed therein so as to pass through in the thickness direction, and a second platform joined to the first platform and having the first chamber, the second chamber, and the fluid passage formed therein.

13. The blood processing apparatus according to claim 9, wherein a plurality of fluid passage sites comprising the first chamber, the second chamber, and the fluid passage are formed in the platform.

14. A method for introducing a blood sample into a chamber having an injection port, an air port, and a blood coagulant held on a periphery of the air port comprising:
introducing blood from the injection port into the chamber so as to cause exhaustion of air in the chamber to an outside of the chamber via the air port; and
bringing the blood sample that have introduced to the chamber into contact with the blood coagulant so as to seal the air port with the blood sample coagulated by the blood coagulant.

15. A method for holding the blood coagulant in the chamber of the blood processing apparatus according to claim 1, comprising:
preparing a solution in which the blood coagulant is dissolved at a predetermined concentration;
dropping the solution on the port wall surface and/or around the portion of the surface of the platform where the air port is open; and
drying the dropped solution.

16. The method for holding the blood coagulant according to claim 15, wherein the dropped solution is dried by lyophilization.

* * * * *